US011893733B2

(12) United States Patent
Ranatunga et al.

(10) Patent No.: US 11,893,733 B2
(45) Date of Patent: Feb. 6, 2024

(54) TREATMENT EFFICACY PREDICTION SYSTEMS AND METHODS

(71) Applicant: OUROTECH, INC., Dover, DE (US)

(72) Inventors: Duleeka Nimantha Bandara Ranatunga, London (GB); Eleonora Peerani, London (GB); Gastón Agustín Primo, London (GB); Zhi Yuan Lin, London (GB); Sacha Hu, London (GB); Aston Martin Crawley, Southampton (GB)

(73) Assignee: OUROTECH, INC., Dover, DE (US)

( * ) Notice: Subject to any disclaimer, the term of this patent is extended or adjusted under 35 U.S.C. 154(b) by 0 days.

(21) Appl. No.: 17/511,125

(22) Filed: Oct. 26, 2021

(65) Prior Publication Data
US 2023/0010963 A1    Jan. 12, 2023

Related U.S. Application Data

(63) Continuation of application No. PCT/US2021/054411, filed on Oct. 11, 2021.
(Continued)

(51) Int. Cl.
*G06T 7/00* (2017.01)
*G01N 1/30* (2006.01)
(Continued)

(52) U.S. Cl.
CPC ............ *G06T 7/0012* (2013.01); *C12N 1/04* (2013.01); *G01N 1/30* (2013.01); *G01N 33/5091* (2013.01); *G01N 33/582* (2013.01); *C12N 2513/00* (2013.01); *C12N 2533/54* (2013.01); *C12N 2533/80* (2013.01); *G06T 2207/30024* (2013.01)

(58) Field of Classification Search
None
See application file for complete search history.

(56) References Cited

U.S. PATENT DOCUMENTS 10,983,116 B2 *  4/2021  Fan ................. G01N 33/54366
2004/0224380 A1  11/2004  Chou et al.
(Continued)

FOREIGN PATENT DOCUMENTS

WO    WO-2014008222 A1 *  1/2014  ............ C12M 33/06
WO    WO2017096232          *  2/2016
WO       2017218202 A1      12/2017

OTHER PUBLICATIONS

U.S. Patent and Trademark Office, "PCT International Search Report and Written Opinion," dated Mar. 1, 2022, for PCT Application No. PCT/US2021/054411, 15 pages.
(Continued)

*Primary Examiner* — Nancy Bitar
(74) *Attorney, Agent, or Firm* — Dorsey & Whitney LLP

(57) ABSTRACT

Systems and methods for predicting a patient response to various agents and/or combinations of agents using ex vivo dosing and imaging are disclosed. In one example, a method of determining treatment efficacy includes analyzing a solid cell culture over time, e.g., first and second responses to a solid cell culture to respective treatments may be compared to determine a treatment efficacy of each treatment. Systems and methods for applying the treatments to the cell culture and analyzing the cell culture and efficacy are disclosed.

29 Claims, 20 Drawing Sheets

Related U.S. Application Data

(60) Provisional application No. 63/219,697, filed on Jul. 8, 2021.

(51) Int. Cl.
  *G01N 33/58* (2006.01)
  *C12N 1/04* (2006.01)
  *G01N 33/50* (2006.01)

(56) References Cited

U.S. PATENT DOCUMENTS

| | | | |
|---|---|---|---|
| 2009/0018033 A1* | 1/2009 | Morgan | C12M 25/00 435/375 |
| 2012/0135452 A1* | 5/2012 | Shuler | C12M 29/00 435/395 |
| 2016/0258931 A1* | 9/2016 | Silva | G01N 15/1475 |
| 2018/0009901 A1* | 1/2018 | Sariel | C07K 16/3046 |
| 2018/0085750 A1* | 3/2018 | Varghese | B01L 3/502707 |
| 2018/0179481 A1* | 6/2018 | Fujimoto | G01N 35/00029 |
| 2019/0119618 A1 | 4/2019 | Iamilton et al. | |
| 2019/0324028 A1* | 10/2019 | Fan | G01N 33/54366 |
| 2020/0284730 A1* | 9/2020 | Su | G01N 21/6452 |
| 2020/0392440 A1* | 12/2020 | Nieh | C12M 41/46 |
| 2021/0092555 A1* | 3/2021 | Mayor | G06K 9/629 |

OTHER PUBLICATIONS

Fiorini et al., "Modeling Cell Communication in Cancer with Organoids: Making the Complex Simple," Frontiers in Cell and Developmental Biology, (2020), 8:1-12.

Robertson et al., "Imaging and Analysis of 3D Tumor Spheroids Enriched for a Cancer Stem Cell Phenotype," Journal of Biomolecular Screening, (2010) 15(7):820-829.

Serioli et al., "Bacterial Cell Cultures in a Lab-on-a-Disc: A Simple and Versatile Tool for Quantification of Antibiotic Treatment Efficacy," Anal. Chem., (2020), 92(20):3871-13879.

Sokol et al., "Growth of Human Breast Tissues From Patient Cells in 3D Hydrogel Scaffolds," Breast Cancer Research, (2016), 18(19): 1-13.

Sun et al., "Mechanistic adaptability of cancer cells strongly affects anti-migratory drug efficacy," J. R. Soc. Interface, (2014), vol. 11: 1-11.

Walsh et al., "Functional Optical Imaging of Primary Human Tumor Organoids: Development of a Personalized Drug Screen," The Journal of Nuclear Medicine, (2017), 58(9):1367-1372.

Wang, "Stem cells in tissues, organoids, and cancers," Cellular and Molecular Life Sciences, (2019), 76:4043-4070.

Wlodkowic et al., "Cytometry in Cell Necrobiology Revisited. Recent Advances and New Vistas," Cytometry A, (2010), 77(7):591-606.

Thermo Fisher Scientific, "Invitrogen," eBioscience DRAQ5, Catalog No. 65-0880, From the Internet: https://www.thermofisher.com/document-connect/document-connect.html?url=https://assets.thermofisher.com/TFS-Assets%FLSG%2Fmanuals%2F65-0880.pdf, (2017), 2 pages.

Fang et al., "Development and Dynamic Regulation of Mitochondrial Network in Human Midbrain Dopaminergic Neurons Differentiated from iPSCs," ISSCR, Stem Cell Reports, (2016), 7:678-692.

Robinson et al., "The selective detection of mitochondrial superoxide by live cell imaging," Nature Protocols, (2008), 3(6):941-947.

Enderle et al., "Dynamic Imaging of IEL-IEC Co-Cultures Allows for Quantification of CD103-Dependent T Cell Migration," Int. J. Mol. Sci., (2021), vol. 22, 5148, 15 pages. https://doi.org/10.cc90/ijms22105148.

* cited by examiner

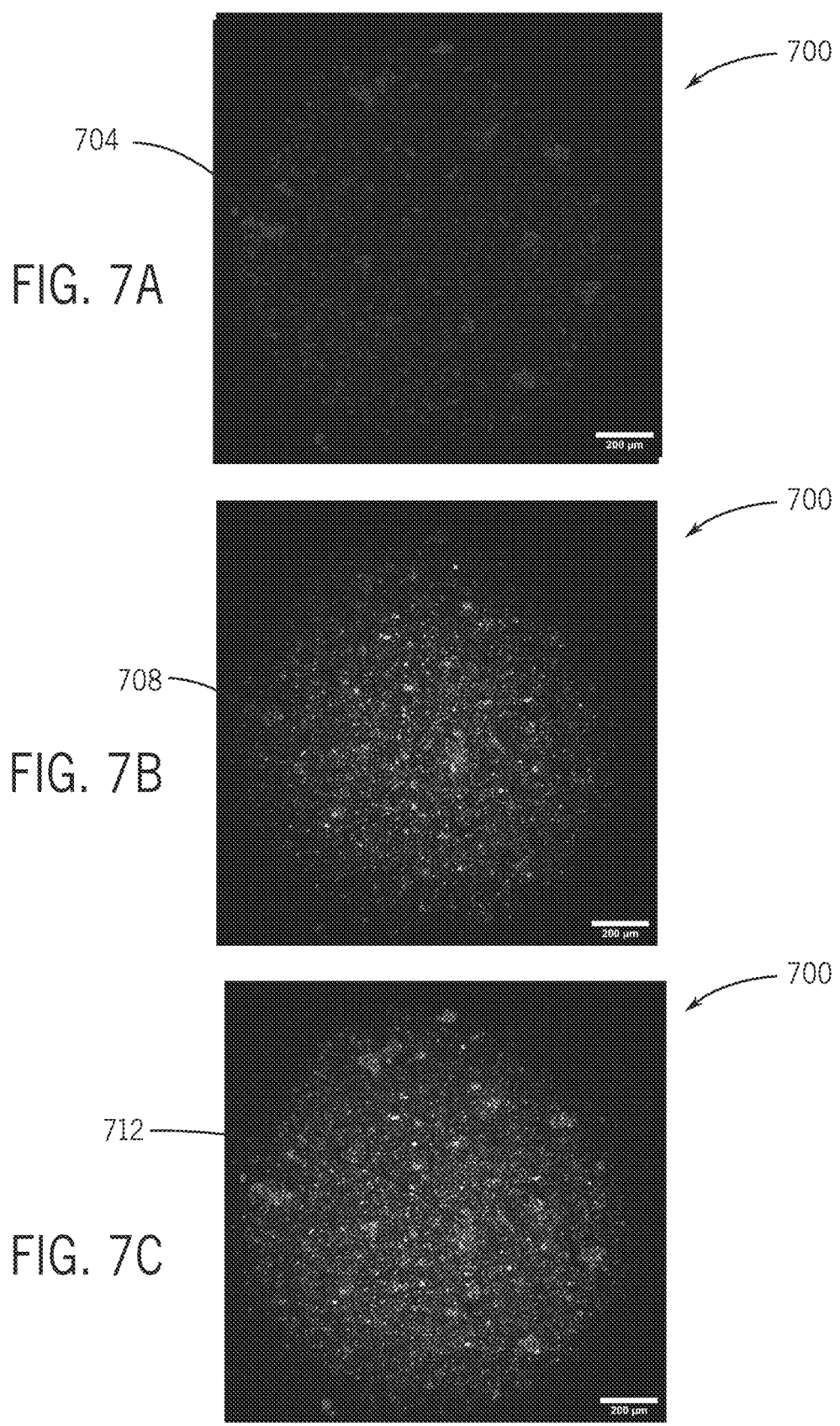

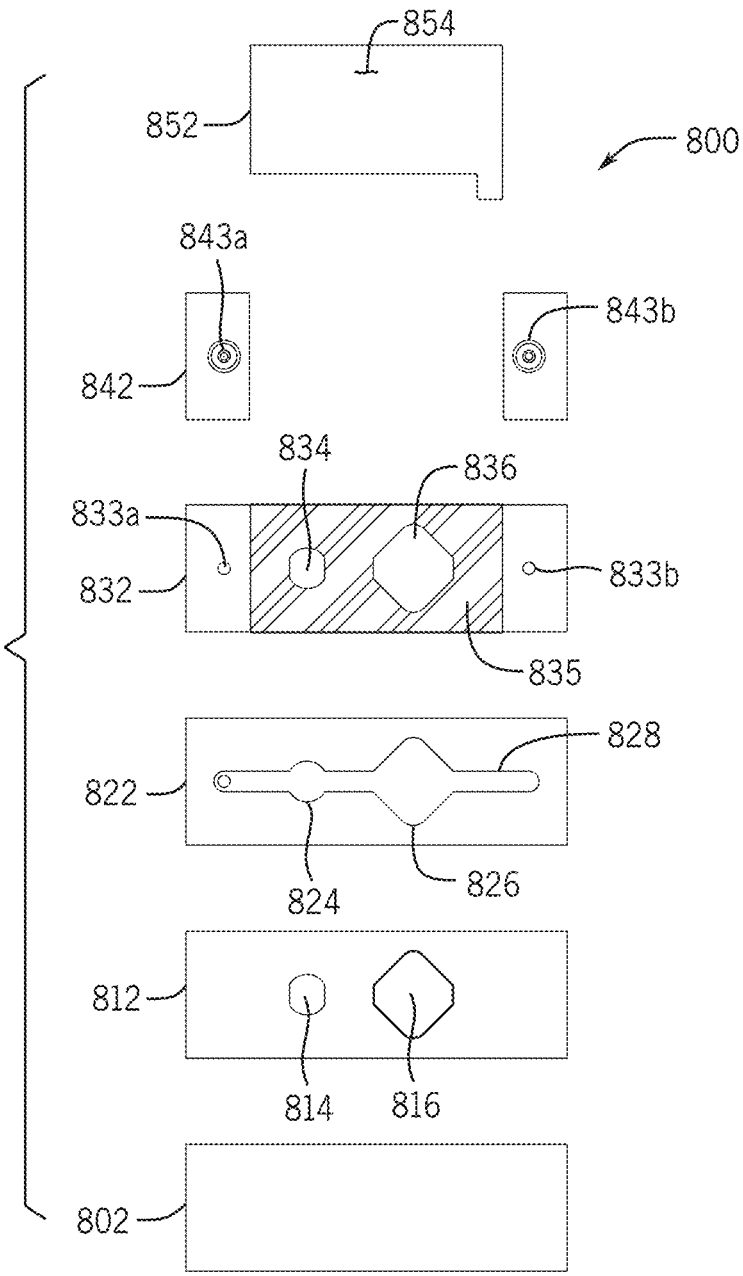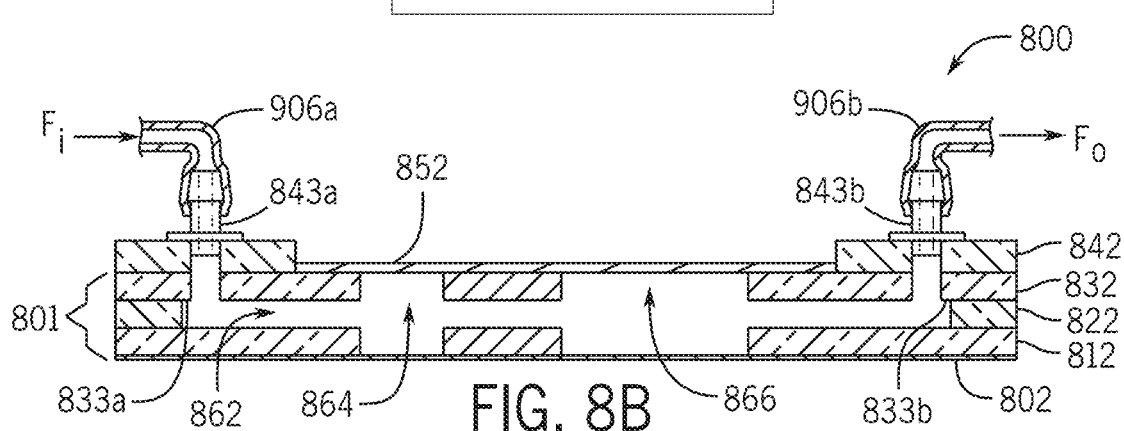

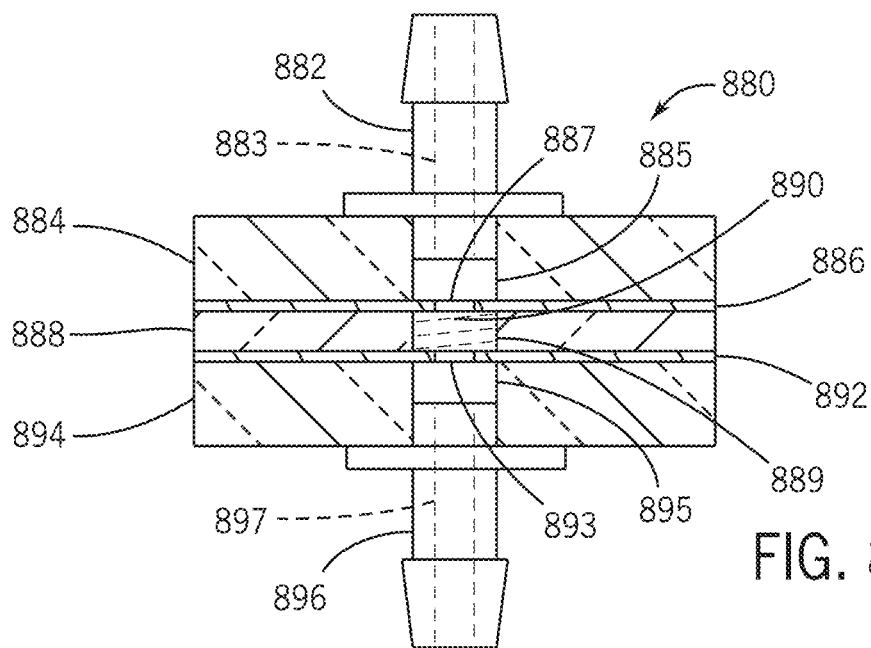
FIG. 8C
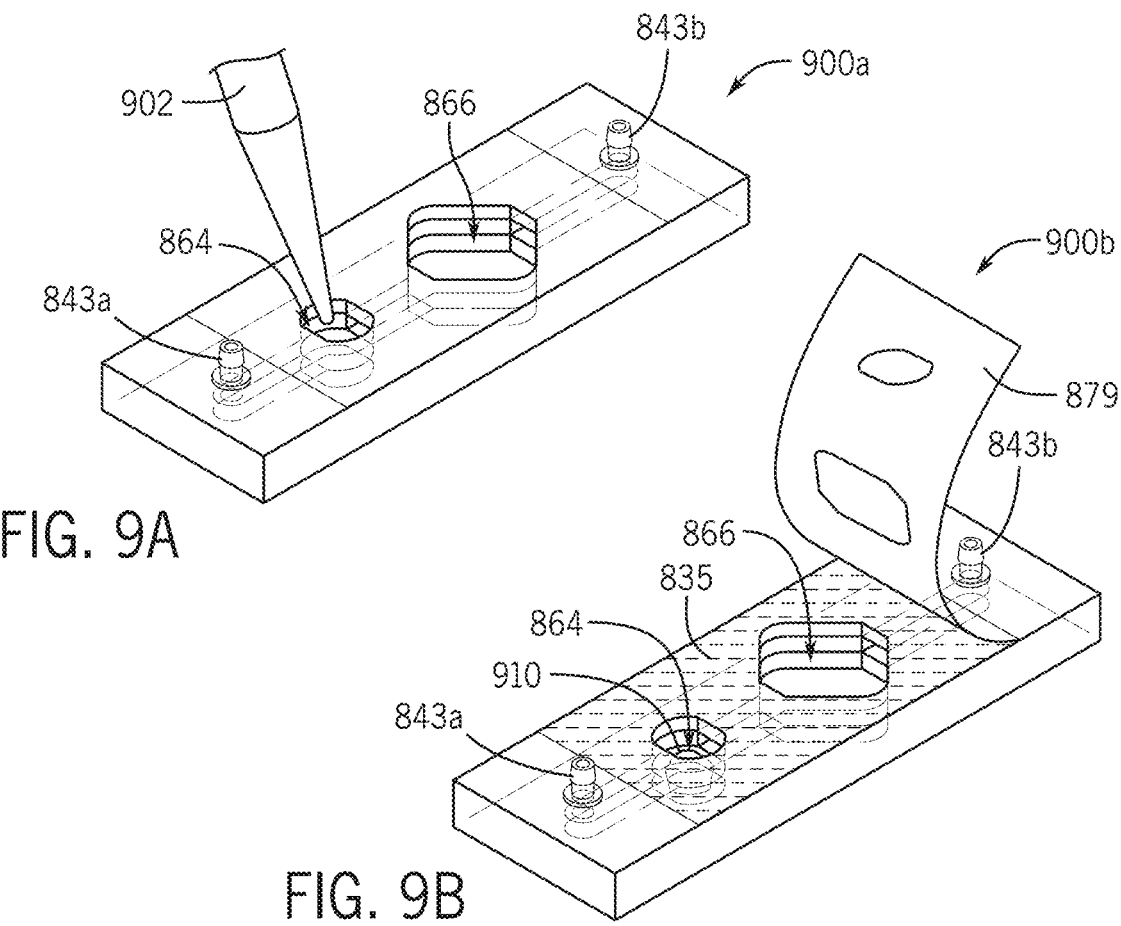
FIG. 9A
FIG. 9B

NUMBER OF LIVING CELLS ON DAY 1

NUMBER OF LIVING CELLS ON DAY 4

TREATMENT EFFICACY PREDICTION SYSTEMS AND METHODS

CROSS-REFERENCE TO RELATED APPLICATIONS

This application claims priority to PCT Application No. PCT/US2021/054411, filed Oct. 11, 2021, entitled "Treatment Efficacy Prediction Systems and Methods," which claims priority to U.S. Provisional Application No. 63/219,697, filed Jul. 8, 2021, entitled "Treatment Efficacy Prediction Systems and Methods," both of which are incorporated herein in their entirety for all purposes.

FIELD

The described embodiments relate generally to systems and methods for determining the efficacy of a treatment, such as an anti-cancer agent.

BACKGROUND

A range of treatment agents, such as anti-cancer agents, may be used to treat cancerous cells, such as those associated with various types of tumors. Factors such as tumor type, progression, patient characteristics, anti-cancer agent characteristics, and so on may impact the efficacy of a given treatment. These and other factors may hinder the ability of a medical provider to select the most appropriate anti-cancer agent, such as that with the highest efficacy. Anti-cancer treatments may be administered that result in a minimal efficacy and/or detract from overall patient treatment. Similarly, other types of treatments for certain diseases may vary for different patients based on specific patient factors. As such, there is a need for systems and techniques to facilitate individualized biomarker discovery, diagnostics and/or prognostics associated with the efficacy of particular medical treatments, such as, treatment with anti-cancer and other treatment agents.

SUMMARY

Embodiments of the present invention are directed to treatment efficacy prediction systems and methods.

In one example, a microfluidic chip is disclosed. The microfluidic chip includes a body defining a channel and a cell culture chamber fluidly coupled to the flow channel. The microfluidic chip further includes a coupling portion attached to the body and defining an inlet and an outlet. The channel defines a flow path extending between the inlet and the outlet with the cell culture chamber positioned therebetween. The microfluidic chip further includes a gas permeable membrane covering the cell culture chamber.

In another example, the channel is configured to deliver a growth media to the cell culture chamber. The cell culture chamber may have a substantially cylindrical shape. For example, the cell culture chamber may have a substantially cylindrical shape with a diameter of preferably about 6.75 mm. In other cases, the diameter may be more or less than 6.75 mm based on the particular application, such as being at least about 5.0 mm, at least about 3.0 mm or other appropriate diameter.

In another example, the body defines the cell culture chamber having a closed bottom end and an open top end. The gas permeable membrane may cover the open top end of the cell culture chamber. Further, the gas permeable membrane may be attached to the body portion by an adhesive.

In another example, the cell culture chamber may be a first cell culture chamber. In this regard, the body may further define a second cell culture chamber fluidly coupled to the channel along the flow path between the first cell culture chamber and the inlet or the outlet of the coupling portion. The first cell culture chamber may have a first volume and the second cell culture chamber may have a second volume that is different from the first volume; however, this is not required. Further, the first cell culture chamber may have a first shape and the second cell culture chamber may have a second shape that is different from the first shape; however, this is not required.

In another example, the body includes a multi-layered structure. In this regard, the multi-layered structure includes a first body portion layer defining the cell culture chamber. The multi-layered structure further includes a second body portion layer connected to the first body portion layer and defining the channel fluidly coupled to the cell culture chamber. The multi-layered structure further includes a third body portion layer connected to the second body portion layer opposite the first body portion layer and defining an opening or hole above the cell culture chamber. In some cases, the coupling portion may be attached to the third body portion layer. As such, the third body portion layer further defines a first lumen fluidly coupled to the inlet of the coupling portion and extending to the flow channel of the second body portion layer. The third body portion may further define a second lumen fluidly coupled to the outlet of the coupling portion and extending to the flow channel of the second body portion layer.

In another example, the inlet and the outlet define tube barbs. The barbs may protrude from a topmost surface of the chip. While many material constructions are possible, the body may include or be formed fully from an acrylic material or a silicone-based material.

In another example, a microfluidic device is disclosed. The microfluidic device may include a dosing bank including a plurality of reservoirs. Each reservoir of the plurality of reservoirs may be configured to hold a growth media. The microfluidic device may further include a staging section or "stage" configured to arrange a plurality of microfluidic chips. The plurality of reservoirs can correspond to the plurality of microfluidic chips. In some cases, multiple reservoirs may be used for any given microfluidic chip. The microfluidic device may further include a pump fluidly coupleable with the plurality of reservoirs and the plurality of microfluidic chips to define fluid circuits between each corresponding pair of the plurality of reservoirs and the plurality of microfluidic chips. The pump further may cause a circulation of a growth media through the fluid circuits for each corresponding pair.

In another example, each reservoir of the plurality of reservoirs are fluidly isolated from one another. The fluid circuits may therefore be fluidically isolated from one another. The pump may be further configured to selectively cause a circulation of the growth media through an individual fluid circuit of the fluid circuits. The growth media may include a treatment agent, such as an anti-cancer agent and/or cells in suspension. In this regard, the cells may be in circulation with the growth media such that the drugs, cells, and/or other agents are included. In some cases, circulating cells can be used to make immune models or test cell therapies. Additionally or alternatively, other circulating agents can help characterize the behavior or properties of the cells in circulation.

In another example, the plurality of reservoirs may be exposable to atmosphere. For example, the reservoirs may have lids that can be opened to expose the reservoir to air for the purpose of loading treatments. Once the treatment is loaded, the lid can be closed. The microfluidic device may operate as described herein upon the closing of the reservoirs with the lids. In this regard, the plurality of reservoirs may be configured to receive a treatment agent or combination of agents during operation of the pump.

In another example, the dosing bank may include a tray or other structure configured to hold the plurality of reservoirs in a substantially upright position. The device may further include tubes fluidly coupling the pump to each reservoir and each microfluidic chip housed in the staging section.

In another example, a method of forming a solid culture is disclosed. The method includes isolating target cells from a patient sample. The method further includes forming stained cells from the isolated cells by staining the isolated cells with a light-responsive dye. The method further includes encapsulating the stained cells in a hydrogel. In one example, the hydrogel may include hyaluronic acid, collagen and/or other elements that are configured to mimic core components of human tissue extracellular matrices and/or disease-specific cell niches.

In another example, the method may further include culturing dissociated cells in the hydrogel. The culturing may further include forming two-dimensional cell cultures of the dissociated cells. The culturing may further include forming three-dimensional cell cultures of the dissociated cells. The culturing may further include forming cell cultures of a single population of dissociated cells. The culturing may further include forming cell cultures from multiple cell types.

In another example, the dissociated cells include cancer cells as well as normal/non-transformed cells, stromal cells, or immune cells. In this regard, the culturing further comprises forming co-culture of cancer, normal/non-transformed, stromal, and/or immune cells. The dissociated cells may be isolated from a patient-derived tissue or tumor sample.

In another example, the method may further include forming the spheroid or an organoid. In some cases the method may include culturing the spheroid or the organoid in a hydrogel. The spheroid or the organoid may include cancer cells, normal/non-transformed cells, stromal cells, or immune cells. In some cases, the culturing further includes forming co-culture of cancer, normal/non-transformed, stromal, and/or immune cells. The isolated cells may be isolated from a patient-derived tissue or tumor sample.

In another example, the method further includes processing the patient sample using a digestion enzyme-based operation, a blood lysis solution, or a selecting operation to isolate target cells of the patient sample. Processing may allow for the isolation of many different cell types, such as many different cell types that stay alive from the patient tissue or tumor sample. As such, different cells can be co-cultured, including cells in addition to cancer, normal/non-transformed, immune, and/or stromal cells, in either a dissociate cell culture or spheroid/organoid.

In another example, the light-responsive dye may be configured to allow for tracking of the target cells via fluorescence microscopy. The light-responsive dye may be configured to stain mitochondria of the target cells for live cell tracking. The light-responsive dye may be configured to stain nuclei of the target cells for dead cell tracking.

In another example, forming stained cells further includes staining isolated cells with a first light-responsive dye. The first light-responsive dye may be configured to stain mitochondria of the target cells for live cell tracking. Forming stained cells may further include staining isolated cells with a second light-responsive dye, the second light-responsive dye being configured to stain nuclei of the target cells for dead cell tracking.

In another example, the light-responsive dye may be configured to cause a color change in the stained cell when the stained cell transitions from a living cell to a dead cell. The target cells may be, without limitation, cells of a tumor, the tumor comprising a breast cancer, a colorectal cancer, a lung cancer, a kidney cancer, a pancreatic cancer, an ovarian cancer, a brain cancer, or a gastric cancer.

In another example, the patient sample includes tissue slices, surgical resections and/or xenografts. The patient sample may also include biopsy samples, including core needle biopsy samples in certain circumstances. In this regard, the method may further include culturing the tissue slices, cores, surgical resections and/or xenografts in a hydrogel.

In another example, a method of loading a microfluidic chip is disclosed. The method includes arranging a solid cell culture in a cell culture chamber of the microfluidic chip. The microfluidic chip includes a body defining the cell culture chamber and a channel that traverses the cell culture chamber and extends between an inlet and an outlet of the microfluidic chip. The method further includes positioning a gas permeable membrane over the cell culture chamber while the inlet and outlet remain exposed for coupling to a circulation system.

In another example, the positioning further includes adhering the gas permeable membrane to the body and covering the cell culture chamber. The arranging of the solid cell culture may further include dropping a quantity of the solid cell culture (e.g., the cell culture in a hydrogel) into the cell culture chamber using a pipette.

In another example, the solid cell culture may be a first solid cell culture and the cell culture chamber may be a first cell culture chamber. In this regard, the method may further include arranging a second solid cell culture in a second cell culture chamber of the microfluidic chip. The second cell culture chamber may be defined by the body and fluidly coupled to the channel between the inlet and the outlet. The first cell culture chamber may have a first volume and the second cell culture chamber may have a second volume that is different from the first volume. The first cell culture chamber may have a first shape and the second cell culture chamber may have a second shape that is different from the first shape.

In another example, a method of operating a microfluidic chip is disclosed. The method includes fluidly coupling the microfluidic chip with a microfluidic device to define a fluid circuit between the microfluidic chip, a flow restrictor, a reservoir, and a pump; the microfluidic chip including a solid cell culture, the reservoir including a growth media. The method further includes causing a flow of the growth media through the circuit such that the solid cell culture of the microfluidic chip is exposed to the growth media to form an exposed cell culture. As used herein, a "solid cell culture" refers to the cells in the hydrogel material. An "exposed cell culture" refers to a circumstance in which the solid cell culture is exposed to media (e.g., growth media) while the cell culture itself remains solid (e.g., the growth media flowing along the hydrogel with cells). As further used herein, a "liquid cell culture" refers to cells that are in a liquid medium exclusively. For example, a liquid cell culture may include immune cells put into a growth media/serum and then circulated using the systems and techniques described herein. The method includes analyzing a response of the solid cell culture to the growth media.

In another example, the growth media includes a treatment agent. In some cases, the fluid coupling further includes fluidly coupling a first tube portion to an inlet of the microfluidic device. The first tube portion may be connected to a second tube portion fluidly coupled with a reservoir, the first and second tube portions defining a common tube. The fluid coupling may further include fluidly coupling a third tube portion to an outlet of the microfluidic device and the reservoir to define a fluid circuit. The microfluidic device may define a flow path therethrough.

In another example, the microfluidic chip may include a cell culture chamber that holds the hydrogel including the target cells. The flow path may traverse and/or run adjacent to the cell culture chamber. The method may therefore further include causing a flow of the growth media along the flow path while a hydrogel restrains the target cells from exit from the culture cell culture chamber.

In another example, the first tube portion may be fluidly coupled to the pump. The second tube portion may be fluidly coupled to the reservoir. The first and second tube portions may be portions of the same tube. The microfluidic device may further include a third tube portion connected to the reservoir and the microfluidic chip to complete the circuit. The circuit may be a closed-circuit.

In another example, the method further includes fluidly coupling a second microfluidic chip with the microfluidic device to define a second fluid circuit between the second microfluidic chip, a second reservoir, and the pump; the second microfluidic chip including a second solid cell culture, the second reservoir including a second growth media. The method may further include causing a second flow of the second growth media through the second circuit such that the second solid cell culture of the second microfluidic chip is exposed to the second growth media. The method may further include analyzing a response of the second solid cell culture to the second growth media.

In another example, the growth media and the second growth media include different treatment agents, such as different anti-cancer agents or cells. The method may further include comparing the response of the first solid cell culture and the response of the second solid cell culture to determine a treatment efficacy. The first circuit and the second circuit may be fluidly isolated from one another. In this regard, the pump may be configured to control the first flow and the second flow independently.

In another example, the method may further include, prior to the analyzing, fluidly uncoupling the microfluidic chip from the microfluidic device. In this regard, subsequent to the analyzing, the method may further include fluidly coupling the microfluidic chip with the microfluidic device to define the fluid circuit between the microfluidic chip, the reservoir, and the pump. The method may further include causing another flow of the growth media (e.g., the same growth media or a different growth media) through the circuit such that the solid cell culture of the microfluidic chip is exposed to the growth media. The method may further include, subsequent to the causing of another flow, analyzing a subsequent response of the solid cell culture to the growth media.

In another example, the method may therefore further include comparing the response of the solid cell culture to the growth media and a subsequent response of the solid cell culture to the growth media to determine a treatment efficacy. The method may further include analyzing the response of the solid cell culture to the growth media to determine a first cell population quantity. The method may further include analyzing the subsequent response of the solid cell culture to the growth media to determine a second cell population quantity. As described herein, the method may further include analyzing further subsequent responses of the solid cell culture and determining a third cell population quantity, a fourth cell population quantity, and so one over a course of days or other appropriate interval. The method may further include comparing the first cell population quantity and the second cell population quantity to determine a change in cell population quantity indicative of a treatment efficacy. In this regard, the method may further include analyzing the response of the solid cell culture to the growth media to determine a first cell population position, and analyzing the subsequent response of the solid cell culture to the growth media includes determining a second cell population position. As described herein, the method may further include analyzing further responses of the solid cell culture and determining a third cell population position, a fourth cell population position, and so one over a course of days or other appropriate interval. The method may further include comparing the first cell population position and the second population position to determine a change in cell population position indicative of a treatment efficacy.

In another example, the analyzing may include conducting a fluorescence microscopy operation on the solid cell culture of the microfluidic chip. In some cases, the analyzing includes collecting three-dimensional images of the solid cell culture of the microfluidic chip. The analyzing may further include collecting two-dimensional images in a z-stack of the solid cell culture of the microfluidic chip. The analyzing may further include analyzing multiple responses of the solid cell culture to the growth media over time. The analyzing may be conducted daily.

In another example, the analyzing may include conducting a confocal microscopy operation on the solid cell culture of the microfluidic chip. Additionally or alternatively, the analyzing may include conducting a brightfield microscopy operation on the solid cell culture of the microfluidic chip. Additionally or alternatively, the analyzing may include conducting a lattice light sheet microscopy operation on the solid cell culture of the microfluidic chip.

In another example, the analyzing includes executing instructions of a non-transitory computer-readable media, with one or more processing elements of a computer, to determine a treatment efficacy of a treatment agent of the growth media, on the solid cell culture.

In another example, a method of analyzing a solid cell culture over time is disclosed. The method includes determining a first response of a solid cell culture to a growth media including a treatment agent. The solid cell culture is held in a cell culture chamber of a microfluidic chip. The method further includes determining a second response of the solid cell culture to the growth media, including a treatment agent. The method further includes comparing the first and second responses to determine a treatment efficacy. In some cases, and as described herein, multiple responses of the solid cell culture may be compared to determine treatment efficacy, such as comparing three, four, or more responses for each solid cell culture/chip as appropriate for a given application. In this regard, while the example of comparing a first and second response is presented for purposes of illustration, it will be appreciated that the computer vision and imaging techniques described herein may be applied to comparing and analyzing any number of responses over any appropriate time period.

In another example, one or both of the first response or the second response includes at least one of a color of the solid cell culture, a pixel intensity of an image of the solid cell culture, a shape of the solid cell culture, a size of the solid cell culture, a position of cells of the solid cell culture, or a quantity of cell of the solid cell culture. The treatment efficacy may be indicative of a viability of cells of the solid cell culture in response to the treatment agent.

In another example, determining the first response comprises capturing an image of the solid cell culture. In this regard, the method may further include determining a cell viability from the image and predicting a patient response to treatment agent based on the cell viability. The method may further include determining a cell proliferation from the image and predicting a patient response to treatment agent based on the cell proliferation. The method may further include determining a cell position from the image and predicting a patient response to treatment agent based on the cell position.

In another example, the image may be a first image. In this regard, determining the second response may include capturing a second image of the solid cell culture. The method may further include comparing the first image and the second image (and/or additional images) to determine a cell migration distance of a cell of the solid cell culture over time. The method may further include predicting a patient response to the treatment agent using the cell migration distance.

In another example, the method may further include comparing the first image and the second image to determine a cell migration speed of a cell of the solid cell culture over time. In turn, the method may further include predicting a patient response to the treatment agent using the cell migration speed.

In another example, the method may further include comparing the first image and the second image to determine a migration distance of a plurality of cells that define a subset of the solid cell culture over time. In turn, the method may further include predicting a patient response to the treatment agent using the migration distance.

In another example, the method may further include comparing the first image and the second image to determine a migration speed of a plurality of cells over time. In turn, the method may further include predicting a patient response to the treatment agent using the migration speed.

In another example, with reference to determining a migration distance and/or a migration speed, the subset of cells may include the 5% most aggressive cells of the plurality of cells. In other cases, the plurality of cells may include the 2% most aggressive cells of the plurality of cells. In other cases, the plurality of cells may include the 1% most aggressive cells of the plurality of cells. Additionally or alternatively, the plurality of cells may include the subset of cells expressing a specific biomarker.

In another example, the method may further include comparing the first image and the second image to determine a cell having a maximum migration vector in the solid cell culture over time. In turn, the method may further include predicting a patient response to the treatment agent using the maximum migration vector.

In another example, the method may further include comparing the first image and the second image to determine a cell having a maximum migration speed in the solid cell culture over time. In turn, the method may further include predicting a patient response to the treatment agent using the maximum migration speed.

In another example, one or both of determining the first response or determining the second response include determining characteristics of a single cell of the plurality of cells. The single cell of the plurality of cells may have characteristics that can be used to predict a response of the plurality of cells (e.g., the cell with longest migration vector may be a predictive biomarker, as one example). In this regard, determining the first response includes determining characteristics of the single cell at a first time. Determining the second response includes determining characteristics of the single cell at a second time subsequent to the first time. In turn, the method further includes predicting a patient response to the treatment agent based on a comparison of the measured characteristics of the single cell at the first time and the second time and/or additional times, as described herein.

In another example, one or both of the first image or the second image include a weighted cell measurement of a single cell or a plurality of cells. In turn, the method may further include predicting a patient response to the treatment agent based on the weighted cell measurement. In some cases, the first image comprises a first weighted cell measurement and the second image comprises a second weighted cell measurement. In turn, the method further includes predicting a patient response to the treatment agent based on a comparison of the first weighted cell measurement and the second weighted cell measurement.

In another example, one or both of the first image or the second image includes information associated with a radius or a diameter of a spheroid or an organoid. The method may further include predicting a patient response to the treatment agent based on the radius or the diameter of a spheroid or an organoid. In some cases, the first image includes a first radius or a first diameter of a spheroid or an organoid and the second image includes a second radius or a second diameter of the spheroid or an organoid. In turn, the method further includes predicting a patient response to the treatment agent based on a comparison of the first radius or the first diameter with the second radius or the second diameter. In some cases, dissociated/single cells may be analyzed in a similar manner. For example, dissociated/single cells may be tracked or measured or otherwise measured according to substantially any of the associated metrics, as described herein. As illustrative examples, a count and/or a position of a dissociated/single cell that leaves the spheroid, a migration distance, a migration speed, and so on may be determined and analyzed according to the techniques described herein for determining treatment efficacy.

In another example, one or both of the first image or the second image includes information associated with one or more of a length, a width, or a height of a surgical resection, tissue slice and/or xenograft. The method further includes predicting a patient response to the treatment agent based on a length, a width, or a height of a surgical resection, tissue slice and/or xenograft. In some cases, the first image includes a first length, a first width, or a first height of an surgical resection, tissue slice and/or xenograft and the second image includes a second length, a second width, or a second height of the surgical resection, tissue slice and/or xenograft. In turn, the method further includes predicting a patient response to the treatment agent based on a comparison of the first length, the first width, or the first height with the second length, the second width, or the second height.

In another example, comparing further includes executing instructions of a non-transitory computer-readable media, with one or more processing elements of a computer, to determine the treatment efficacy.

In addition to the exemplary aspects and embodiments described above, further aspects and embodiments will become apparent by reference to the drawings and by study of the following description.

BRIEF DESCRIPTION OF THE DRAWINGS

FIG. 7A depicts a first representation of an ovarian tumor indicative of living cells.

FIG. 7B depicts a second representation of the ovarian tumor of FIG. 7A indicative of dead cells.

FIG. 7C depicts a third visual representation of the ovarian tumor of FIG. 7A including a composite of living and dead cells.

FIG. 8A depicts an exploded view of an example microfluidic chip.

FIG. 8B is a cross-sectional view of the microfluidic chip of FIG. 8A.

FIG. 8C is a cross-section view of a flow restrictor for use with the microfluidic chip in a fluid circuit.

FIG. 9A depicts an operation of the microfluidic chip of FIG. 8A.

FIG. 9B depicts another operation of the microfluidic chip of FIG. 8A.

DETAILED DESCRIPTION

Figure 1:
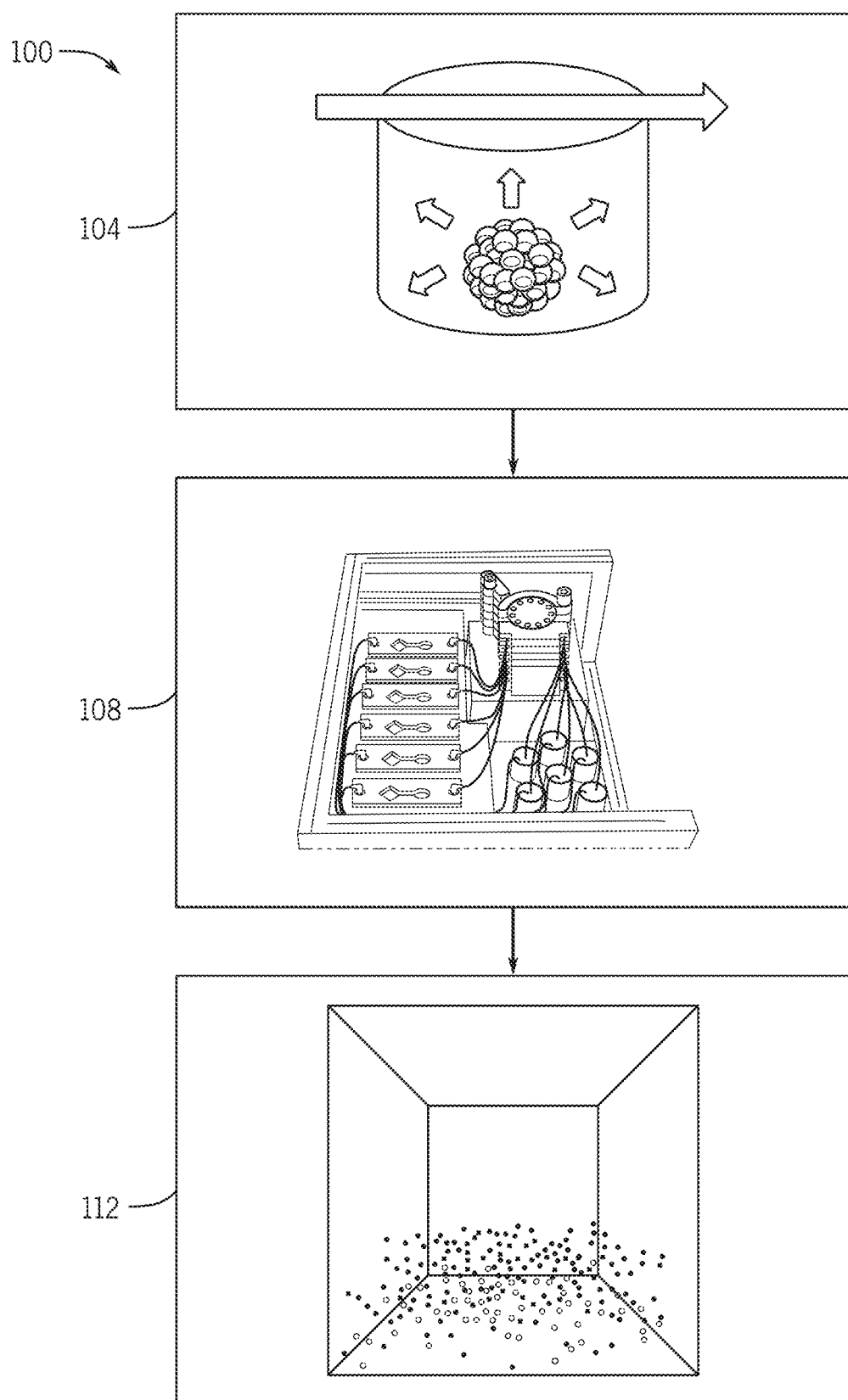
FIG. 1 depicts a functional diagram of a treatment efficacy prediction system.

The description that follows includes sample systems, methods, and apparatuses that embody various elements of the present disclosure. However, it should be understood that the described disclosure may be practiced in a variety of forms in addition to those described herein.

The present disclosure relates to systems and methods for predicting a patient response to various agents and/or combinations of agents using ex vivo dosing and imaging. In some examples, the systems and methods may be applicable to oncology, ex vivo monitoring of disease progression, such as cancer progression, testing of treatment agents, such as anti-cancer agents, patient stratification, and other medical treatment efficacy testing. The system and methods allow discovery, identification, or validation of therapeutic, diagnostic and/or prognostic biomarkers for the purpose of drug development and treatment decision making.

In one embodiment, an organ-on-a-chip and computer vision system are used to analyze biomarkers for predicting patient response to treatment agents, such as anti-cancer agents. In an example implementation, tumor and/or healthy tissue samples may be cultured in a hydrogel or other environment and placed in a cell culture chamber of a microfluidic chip. Tumor and/or healthy tissue samples may be split into multiple segments, such as aliquots, to culture in multiple chips or separate cell culture chambers. The samples are labelled or stained for tracking, such as via light-responsive dyes, such as fluorescent dyes. As described herein, the stained cells may be tracked by microscopy and processed and analyzed by a variety of computer-implemented techniques, such as the disclosed computer vision techniques of the present disclosure. The fluorescent dyes may selectively stain live cells. Other fluorescent dyes selectively stain dead cells. Some dyes may stain all cells, regardless of whether they are alive or dead. In some cases, dyes may be used to stain cells that express certain biomarkers or targets, such as certain proteins. DNA or RNA may also be stained using dyes according to the techniques disclosed herein.

The microfluidic chip, including a cell culture chamber, may be arranged with (e.g. fluidly coupled with) a microfluidic device or other system or pump in order to introduce growth media, treatment agents, and other media to the cell culture of the chip. For example, the device may include various treatment agents held in reservoirs with growth media. The media is circulated from the cell culture chamber to the microfluidic chip using a pump, such as a peristaltic pump, pneumatic pump, and so on. A solid cell culture including target cells and hydrogel may be deposited in the microfluidic chip. The solid cell culture may be exposed to the circulating media, which may include the treatment agents, in order to define an exposed solid cell culture within the microfluidic chip. The cell culture chamber of the microfluidic chip having the solid cell culture may be imaged using various techniques, such as microscopy techniques, including confocal microscopy, to track the live and dead cells over time. The imaging may be based on identification of the cells due to staining or labeling of the cells. For example, the live/dead status of the cells may be tracked using the fluorescent dye or other tracking dye. Three-dimensional (3D) images, or stacks of two-dimensional (2D) images taken layer-by-layer, are collected for analysis using a computer vision tool.

The computer vision tool, which may be executed by one or more computing devices (e.g., via software executing one or more algorithms or machine learning models) may track cell characteristics (e.g., the shape, size, position (x, y, z) and color) of cells in a given image. As the cells may be stained with selectively activated dyes, the number of live and dead cells in an image may be determined. For example, the computer vision may analyze pixel information, such as hue, intensity, and the like, to determine location of specific cells (e.g., live cells may have a first color and dead cells may have a second color) and the location and number of the different cells may be tracked by analyzing subsequent images or image frames over time. One or more images captured at different points in time may be used to monitor the progression of malicious cells (e.g., cancer cells) ex vivo and can be used to predict the response a patient may have to a given agent. For example, comparing a first image frame having a live cell in a first location, such as a first pixel, may be compared to a second image frame captured at a second point in time, having a live cell in a different location, where the system may estimate that the cell has migrated or moved from the first location to the second location. The distance may then be determined by analyzing the difference in pixel locations in the image. Various metrics may be derived from these images, including cell viability, distance and speed of cell migration over time. These assessments, used alone or in combination, may be used to predict patient outcomes to a given agent.

Multiple microfluidic chips may be analyzed in parallel to determine treatment efficacy across a range of anti-cancer treatments. In this regard, microfluidic chips exposed to either no agent (baseline) or various single and/or combination agents, such as chemotherapies, a comparison may be made between images to predict patient response. By comparing various agents and/or combinations of agents, the techniques described herein may be used to discover therapeutic, diagnostic and prognostic biomarkers that aid the treating of cancer patients and the development of new therapeutics.

Reference will now be made to the accompanying drawings, which assist in illustrating various features of the present disclosure. The following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

With reference to FIG. 1, a functional diagram of a treatment efficacy prediction system 100 is depicted. The treatment efficacy prediction system 100 may broadly be configured to facilitate the ex vivo monitoring of disease progression, such as cancer progression, testing of treatment agents, and patient stratification. Broadly, the system 100 may include modules, devices, assemblies, sub-assemblies, and so on (described in relation to the examples of FIGS. 3-17) that cooperate with one another to evaluate the efficacy of a selected treatment agent, combination agents and/or other treatments for use in treating a particular patient. It will be appreciated that any of the modules, devices, assemblies, sub-assemblies, and so on may be implemented separately from one another, as described herein. Treatment agents and other agents, more generally, may be more or less effective based on the particularized circumstances of a treatment regimen, patient characteristic, cancer type and progression or stage, in addition to a range of other complex and often interrelated factors. Conventional treatment regimens may lack the ability to appropriately assess these factors, which may result in the delivery of treatment agents that are suboptimal. Often in conventional systems, various treatment agents may be administered and monitored in vivo, which may hinder the treatment of the patient and overall health outcomes. For example, with conventional approaches, it may be impractical or even impossible to determine if a particular cancer treatment would be effective without administering the treatment to the patient and evaluating the patient over an extended period of time. Further, a patient may have an adverse or undesirable outcome to a particular cancer treatment, once administered. And it may take an exceedingly long period of time for a clinician to assess the efficacy of the treatment, during which time, a patient's overall health conditions may deteriorate.

The system 100 depicted functionally in FIG. 1 may mitigate these and other hindrances by allowing for ex vivo monitoring of cancer progression in the context of proposed treatment agents. The system 100 may permit a clinician or other provider to evaluate a spectrum of various different treatment agents for one or more patient samples, such as a sample including a cancerous tumor. The system 100 may allow for the creation of an ex vivo environment for the patient sample that replicates in vivo conditions. For example, target cells, such as any of the cells described herein, may be cultured and encapsulated in a hydrogel in order to provide structural stability to the cells, mechanical properties and microenvironmental cues to mimic physiological environments in human organs. More generally, a modular environment may be provided including a range of cell culture conditions, including conditions in which human serum is present, in order to provide conditions that may be similar to the conditions of the human body. Over a span of time, such as a series of days, the clinician may monitor the progression and response of each tissue sample for each of the treatment agents. As described in greater detail below, the treatment agents with the most appropriate response or most suitable efficacy may be identified for administration to the patient for treatment.

To facilitate the foregoing, FIG. 1 depicts the system 100 broadly including a culture module 104, a dosing module 108, and an analysis module 112. The culture module 104 may generally include various mechanical components, instrumentation, solutions, and devices and so on that are used to prepare a patient sample for evaluation and dosing. While many functions are contemplated and described herein, the culture module 104 may broadly be configured to isolate target cells from a patient sample, form stained cells from the isolated cells, and encapsulate the stained cells in a media. The target cells may be cells from a patient-derived tissue or tumor sample. The target cells may be from tissue slices, cores, surgical resections and/or xenografts. Sample target cells, without limitation, may include cells associated with malicious tissues, such as cells from a breast cancer, a colorectal cancer, a lung cancer, a kidney cancer, a pancreatic cancer, an ovarian cancer, a brain cancer, or a gastric cancer, and so on. The cell culture module 104 may isolate the target cells and stain the cells with the light-responsive dye, such as a fluorescent dye. Staining, such as with a fluorescent dye may stain or tag the entirety of the cell population or stain individual cell populations, or stain individual components of a given cell population, such as a stain on the mitochondria and a separate stain on a nuclei, to allow for tracking of the cell via fluorescence microscopy or other procedures. The stained cells may be encapsulated in a media, such as a hydrogel, thus forming the solid cell culture, in the culture module 104 in order to promote replication of the core components of human tissue. The stained cells may be encapsulated in a media, such as a hydrogel or may be formed as a spheroid or organoid, thus forming the solid cell culture.

The dosing module 108 may generally include various mechanical components, instrumentation, solutions, and devices and so on that are used to administer treatment agents to a cell culture and collect data regarding the response of the culture to the treatment agents. In this regard, the dosing module 108 may include a microfluidic chip that is configured to receive a solid cell culture (e.g., cells and hydrogel). Growth media may be put in circulation with the solid cell culture to define an exposed solid cell culture. The microfluidic chip may hold the cells in the hydrogel and allow for the circulation of treatment agents alongside growth media in a gas permeable environment (e.g., to provide the cell with oxygen). A pump of a microfluidic device of the dosing module 108 may cause circulation of the treatment agents and growth media through the chip. A plurality of chips, each fluidly coupled in a separate closed circuit, may permit the device to circulate different treatment agents to each chip to deposit the treatments within the cell culture chambers to evaluate the efficacy of different treatments. The chips may be analyzed at select intervals, such as daily (for one, two, three, four, five, or more days), and a response to the treatment agent may be determined. As one example, and as described in greater detail below, fluorescence microscopy may be used to determine the concentration of living and dead cells in a given culture, using the light-responsive dye. More generally, and as described herein, any appropriate camera or imaging device may be used. Images may be captured over time, and presented in a two-dimensional and/or three-dimensional format, in order to provide a sufficient data set for analysis of the treatment efficacy.

The analysis module 112 may generally include various computer vision systems (e.g., computer system 2200 of FIG. 22) or image analysis systems, computer implemented techniques, and analysis devices that may be operated to determine the efficacy of treatment of one or more of treatment agents administered to the cells. The light-responsive dye may be used to indicate the concentration of dead cells, living cells, as well as the transition of cells from a living to dead state. The concentration of cells living or dead, over time, may provide an indication of the viability of cancerous cells, as one example, over the course of administration of a particular treatment agent. Properties of the captured images may be further analyzed to predict a treatment efficacy, including, without limitation, cell characteristics, such as a color of the solid or liquid cell culture, a pixel intensity of an image of the solid or liquid cell culture, a shape of solid or liquid cell culture, a size of the solid or liquid cell culture, a position of cells of the solid or liquid cell culture, or a quantity of cells of the solid or liquid cell culture. In some cases, a two-dimensional or three-dimensional image of the cell culture may be generated at multiple different times over the course of ex vivo administration. Using the light-responsive dyes, the images may include particularized information for each cell, including cell position and type. By capturing multiple images over time, the images can be compared to determine various properties, including cell migration, cell migration speed, and cell migration distance. The images can be further analyzed to determine a maximum migration speed and/or a maximum migration vector, among other characteristics. In this manner, the collective images of the ex vivo response of the cells to the treatment agent may be indicative of an in vivo response to the treatment agent, and thus used to predict treatment efficacy.

Figure 2:
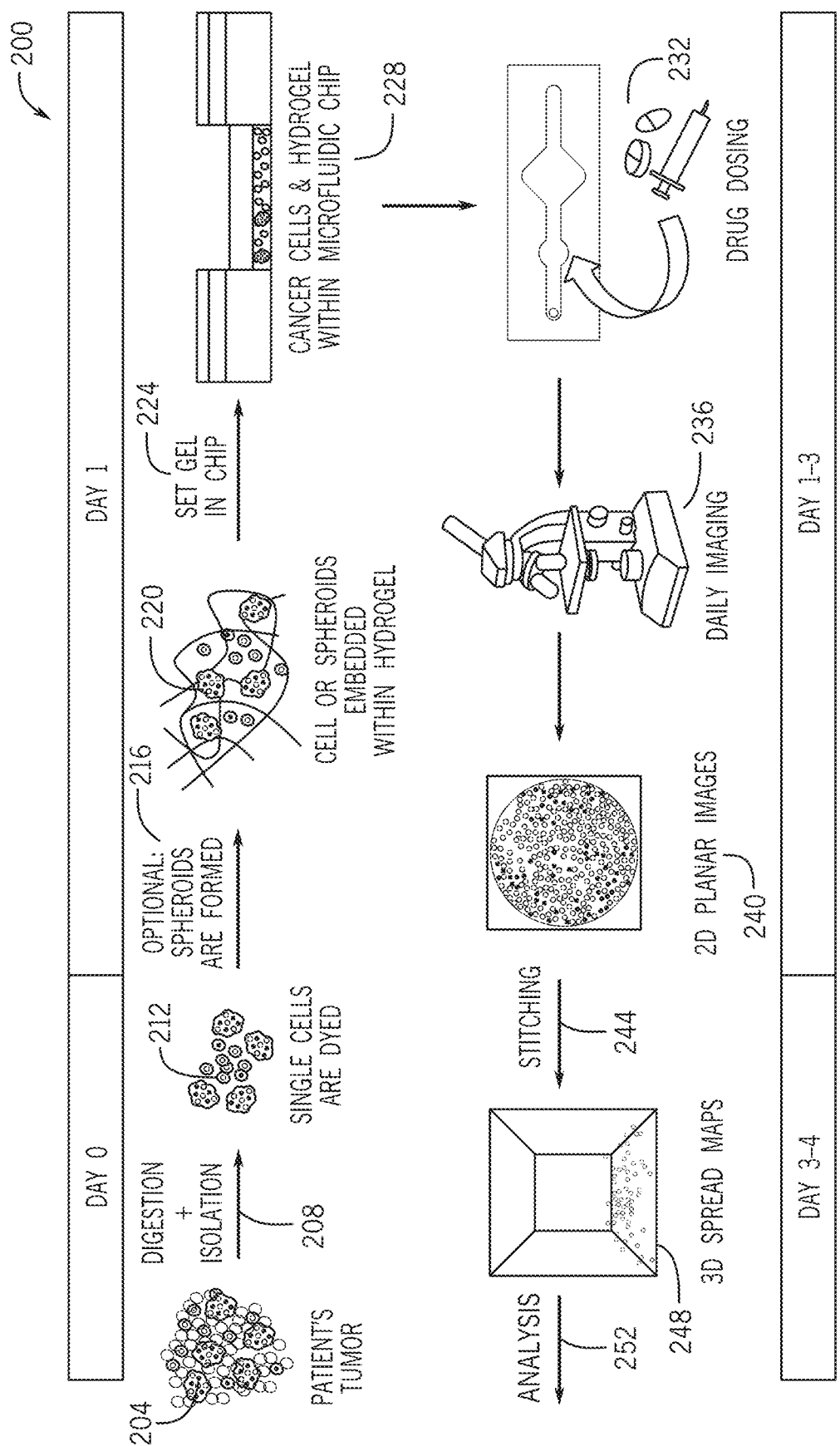
FIG. 2 depicts a flow diagram for determining a treatment efficacy.

FIG. 2 depicts a flow diagram 200 for determining a treatment efficacy. The flow diagram 200 may implement one or more of the operations of the system 100 described above with respect to FIG. 1. Accordingly, the operations described with respect to the flow diagram 200 may be implemented by one or more of the culture module 104, the dosing module 108, and/or the analysis module 112.

At operation 204, a patient sample is collected. Patient samples may arrive at a lab, including samples containing a tumor of various cancer types. At operation 208, tumor samples may be processed using a digestion enzyme-based cell isolation kit, blood lysis solution and other selecting steps to isolate viable cells while removing blood and contaminants. The output may be a viable mixed cell population containing the various cells from the primary tumor, including cancer cells, normal/non-transformed cells, stromal cells, and immune cells.

At operation 212, cells may be stained using live and/or dead cell labeling dyes. Additionally or alternatively, cell-specific/biomarker-targeting dyes may be used. These dyes may be light-responsive dyes that stain or mark the cells. For example, the dyes may be specifically selected for the ability to track cells without requiring the cells to be fixed. In one example, MitoView™ 633 may be used to track live cells by staining the mitochondria of the cells. This dye exhibits a red color when imaged using fluorescence microscopy or other imaging techniques, including confocal and lattice light sheet microscopy. The red color may disappear after cells die. In another example, NucView® 488 may be used to track dead cells by staining the nucleus of the cells. The dye may have a green color when imaged using fluorescence microscopy or other fluorescent imaging techniques; however, it will be appreciated that substantially any color may be used and the foregoing are provided as illustrative example colors. When cells die, the green color may appear. Additionally or alternatively, cells may be stained with both dyes simultaneously to more accurately track cells as they transition from living to dead. It will be appreciated that the red and green colors are described above for purposes of illustration. More generally the light-responsive dyes described herein may have a range of different colors depending in part on the fluorescent dye used. In this regard, various other colors, intensity of colors, and so may be used for staining the cells and performing one or more analysis operations, such as any of the analysis techniques described herein.

At operation 216, spheroids are optionally formed. As one example, an ultra-low attachment (ULA) plate may be used to form the spheroid. As shown in operation 220, the cells or spheroids may be embedded within hydrogel. The hydrogel may contain hyaluronic acid and collagen to mimic core components of human tissue extracellular matrices and/or disease-specific cell niches. The spheroids may include the target and/or stained cells in a generally spheroid shape which may facilitate the determining of the response of the cells to a treatment agent, for example, by permitting the tracking of spheroid characteristics, including, but not limited to, a size, shape or other properties of the spheroid over time.

At operation 224, the spheroid, dissociated cell culture (e.g., without a spheroid architecture), or other cell culture, including a hydrogel and the stained cells, may be set in a microfluidic chip (e.g., the microfluidic chip 800 of FIGS. 8A and 8B). For example, the microfluidic chip may include one or more cell culture chambers. The solid cell culture may be deposited in a first cell culture chamber with a pipette or other instrument. A flow channel is fluidly connected to the one or more cell culture chambers. The flow channel may allow the microfluidic chip to fluidly couple to a circulation system, as described herein with reference to FIGS. 10 and 11. The microfluidic chip may be configured to permit circulation through the flow channels to promote interaction between a circulated flow and the hydrogel and cells of the chip. At operation 228, the hydrogel and cells are within the microfluidic chip and covered by a gas permeable membrane. For example, to seal the chip, a gas permeable membrane may be positioned over the cell culture chamber and adhered to a body of the chip. Once the gas permeable membrane is positioned over the chip, the cell culture chambers are covered. This may allow growth media to flow into the chip without leaking or overflowing using tubing connected to the chip's inlet and outlet barbs.

At operation 232, drug dosing may commence. Each microfluidic device may include reservoirs that are connected to a corresponding microfluidic chip via tubing. In one instance, a peristaltic pump is used to collect growth media in a 15 mL conical tube or reservoir and circulate the growth media to the inlet of the chip. The growth media may then travel through the flow channel and exit through the outlet of the chip. The growth media then returns to the reservoir using another line of tubing. There may be a hermetic seal placed on the reservoir lid and filters placed in the chip inlet and/or outlet to ensure sterility against bacterial and/or microbial contamination.

By running multiple chips/cell culture chambers in parallel, various chemical agents, including chemotherapies, can be tested in parallel. In one instance, six chips/reservoirs may be connected using the peristaltic or other pump. (e.g., FIGS. 10 and 11). One chip may be a control where only growth media is circulated to the dissociated cell culture in the circular chamber. Various drugs and combinations may then be circulated to the other chips via their corresponding cell culture chambers, including Olaparib, AC-T and AC-CarboTaxol. In the case of sequential combination therapies like AC-T and AC-CarboTaxol, a clearing process is in place to initially dose AC, clear out the drug from the cell culture chamber, then add in fresh media containing the Taxol or CarboTaxol for the next round of dosing.

At operation 236, imaging may commence. The imaging may be periodic, such as being at select intervals, such as daily, every twelve hours, and so on as appropriate for a given application. In the present example, the imaging may occur on a daily basis. In this regard, on a daily basis, the media is cleared from the microfluidic chips. The microfluidic chips may be detached from the microfluidic device so they can be transferred to a microscope for imaging. In one instance, a confocal microscope is used to conduct three-dimensional fluorescence imaging. Each chip has the length and width of a standard microscope slide to ensure compatibility. The chips are placed in the slide holder of the confocal microscope and the laser settings are selected to match the excitation wavelength and detection wavelength of each cell staining dye.

In operation 240, two-dimensional images of the chips are captured. For example, the confocal microscope may take images layer by layer from the bottom to the top of the chamber. In one instance, a step size of 5 micrometers may be used. It will be appreciated that in other cases, other steps sizes may be appropriate, such as a step size of 10 micrometers or more. The chamber(s) containing cells may be imaged in its entirety to capture the location of all cells. For example, the circular chamber may be imaged on a daily basis. In other instances, imaging is conducted at larger intervals (e.g., day 1 and day 5), and can also be conducted in shorter intervals (e.g., hour 1 and hour 12). Between each imaging of the chip, the chip may be recoupled with the microfluidic device in order to provide additional treatment agents to the chip. Accordingly, the subsequent imaging of the chip may indicate the progression and response of the tumor to the treatment agent over time.

At operation 244, the two-dimensional images may be stitched together. For example, the raw microscope images may be ordered by their z position. Once the images are ordered from the bottom to the top, each layer can be stitched onto each other along the z axis. Cells are detected on each two-dimensional image and assigned an x, y and z position. In this regard, and as reflected by operation 248, three-dimensional images and other visual representations of the cells may be generated in order to determine a treatment efficacy. For example, once the z-stack is complete, some cells may appear on more than one stack due to the confocal microscopy capturing the same cell in more than one layer. When cells have the same x and y position and appear more than once in adjacent layers on the z axis, the brightest pixel is identified as the true z position of the cell, and optionally may be the only pixel displayed in the final three-dimensional reconstruction. The final three-dimensional reconstruction contains every detected cell with an x, y and z coordinate. In one example, these duplicate cells may be identified through machine learning techniques, such as K-nearest neighbor (KNN) and other techniques. This process can result in the removal of duplicate cells across multiple Z positions in the z-stack. In some cases, such machine learning techniques may also be configured to match multiple stained mitochondria to the same cell. Deep learning and other associated techniques of the computer vision system described herein may also be used. Accordingly, where the cell has multiple mitochondria, the techniques described herein may be used to account for the multiple mitochondria in order to obtain a more accurate cell count.

More broadly, the process 200 may include further analysis operations 252 associated with the analysis of two-dimensional and three-dimensional images and response of the cells to a treatment agent. The analysis operations 252 may be performed using the computer vision and associated systems described herein, such as those described in greater detail below with respect to FIGS. 13A-16. In some cases, the operations may include executing instructions of a non-transitory computer-readable media, with one or more processing elements of a computer, such as the computing system 2200 of FIG. 22. For example, a computer vision tool is disclosed herein that is configured to identify the color of each cell based on the light-responsive or fluorescent dye. Since each cell is treated as a unique object, the color of each cell can also be changed (e.g., all red cells can be changed to blue, or a subset can be changed to blue based on their position or size).

In some cases, an array may be configured to store data on each cell, such as the coordinates and color of each cell, for analysis between multiple time points. Data at a first time point may be indicative of a first response of the cell culture to a treatment agent (e.g., at a first time). Data at a second time point may be indicative of a second response of the cell culture to the treatment agent (e.g., as a second time, subsequent the first time). For example, cells with red fluorescence from MitoView™ 633 may be counted to determine the number of live cells on a first day (e.g., day 1), then compared to an image of the same sample on a later day (e.g., day 5) to determine how many cells died between the first day and the later day. Attributes of cells, such as the average z position of the cells may be calculated on both the first day and the later day to determine, for example, average upward or downward migration of cells between the first day and the later day. Various other cell metrics may be analyzed to determine a change over time as cells are exposed to a drug or combination of drugs.

In another example, disclosed herein is a computer vision analysis system configured to determine at a single-cell level the behavior of each cell over time. The computer vision analysis system may be further configured to analyze the single-cell level behavior to differentiate cancer cells from immune or other cells. In some cases, the computer vision analysis system may be further configured to identify and differentiate among sub-types of cancer cells.

To facilitate the foregoing, deep learning, including using neural networks, can be used to make predictions regarding cells and groups of cells. For example, deep learning can allow for the classification of cells by type (e.g., cancer, stromal or immune). More generally, machine learning can also be used to support one or more of the analysis functions described herein. Further machine learning methods such as K-means and support vector machines (SVMs) may be used to classify single cells and groups of cells. With high resolution and magnification microscopy, cells can be differentiated by their size and shape, and/or various other cell characteristics. As one illustration, a KNN algorithm is used to match a single cell between the first day and the later day (e.g., day 1 and day 5). In this regard, the migration vector of each cell may then be visualized using a quiver plot (e.g., FIG. 15 herein). The sum of the vectors may indicate various trends, such as the total movement of cells in a sample. A subset of vectors (e.g., the top 10%) or individual vectors can be used to help make predictions of patient response to a given treatment.

A combination of metrics extracted from the image data may be used to predict patient response to various treatments, including single agents and combination drugs. In its simplest form, thresholds are set to classify treatment responses using a single metric, such as cell viability, cell migration vector total, or largest single cell migration vector. Simple classifiers, receiver operating characteristic (ROC) curves and logistic regression are example methods of correlating single metrics in the invention to patient response.

The metrics outputted by the computer vision process can be used as input features to perform various predictions. As one example, decision trees may be used to make predictions about the patient outcome using a complex decision making process correlating multiple patient response features. In some cases, decision trees may be used for complex weighing of multiple inputs to optimize prediction accuracy. Training data may be used to correlate inputs to patient response and determine which inputs have the highest impact on predicting patient outcomes. The decision tree may have multiple nodes and branches to facilitate the predictions of a patient response. The final node of the tree (the prediction) may be either the patient's predicted response likelihood or the optimal predicted treatment or even both. Further, the decision tree may be optimized to maximize sensitivity and specificity on a population of patients. The decision tree may also be optimized to maximize positive predictive value and negative predictive value. For example, on a per patient basis, for each proposed treatment, a predicted response with the decision tree (e.g., complete, partial or no response) can be outputted.

With reference to FIGS. 3-17, example implementations of the system 100 of FIG. 1 and process 200 are presented herein. For example, mechanical components, instrumentation, solutions, devices, user interfaces, charts, computing devices, and so on are described for purposes of illustration, which may be used to execute one or more of the functions or techniques described above with respect to FIGS. 1 and 2. It will be appreciated, therefore, that the examples of FIGS. 3-17, rather than limit the disclosure, assist in illustrating various features and functions of the present disclosure. In this regard, other mechanical components, instrumentation, solutions, devices, user interfaces, charts, computing devices, and so on are contemplated herein for implementing the functions and techniques described above in the system 100 and the process 200.

Figure 3:
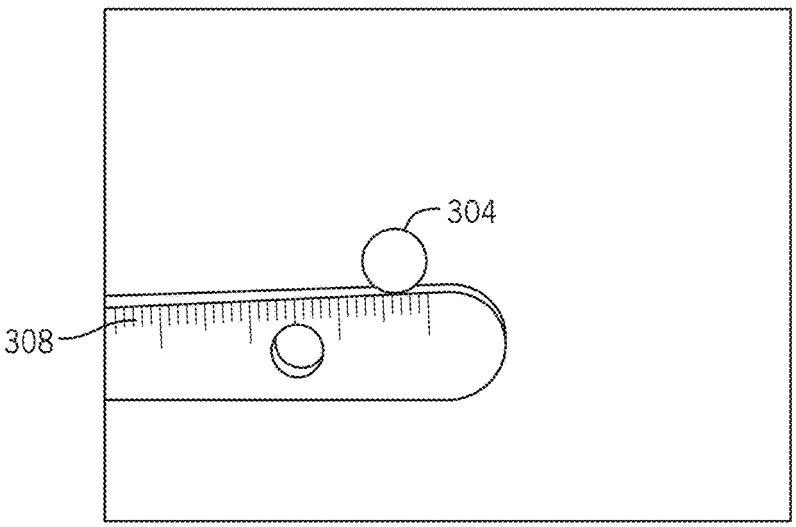
FIG. 3 depicts an example patient sample.

With reference to FIG. 3, an example patient sample 304 is shown relative to a measurement device 308. The patient sample 304 may be a patient-derived tumor sample that is obtained during the operation 204 described above with respect to FIG. 2. The patient sample 304 may include cells of or associated with a malignant tissue, such as cells of a breast cancer, a colorectal cancer, a lung cancer, a kidney cancer, a pancreatic cancer, an ovarian cancer, a brain cancer, or a gastric cancer, among other cancers. The patient sample 304 may include tissue slices, cores, surgical resections, xenografts and/or core needle biopsies. More broadly, the patient sample 304 is shown as being substantially any patient-derived sample collected with respect to the culture module 104 described above. In this regard, the patient sample 304 may include target cells that are arrangeable in a culture for dosing and analysis by the dosing module 108 and the analysis module 112. Accordingly, the patient sample 304 may include dissociated or isolated cells. The patient sample 304 shown in FIG. 3 may be representative of a patient sample prior to forming a solid cell culture or otherwise modifying the patient sample. The sample 304 may therefore further include cancer cells, normal/non-transformed cells, stromal cells, or immune cells. The sample 304 may also include blood and other contaminants, which as described herein, may be selected or filtered or removed using a digestion enzyme-based operation, a blood lysis solution, or a selecting operation among other possibilities.

Figure 4:
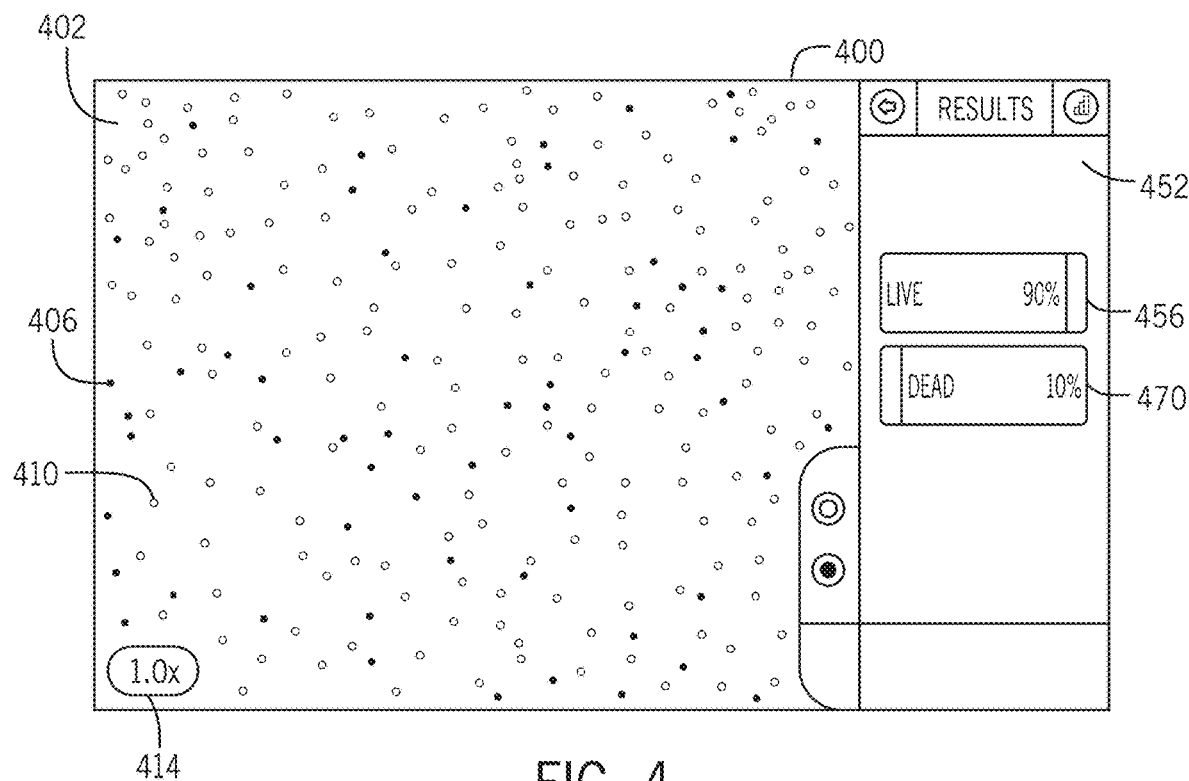
FIG. 4 depicts a user interface including information associated with stained cells.

With reference to FIG. 4, a user interface 400 is depicted including information associated with cells tagged with a tracking dye. The user interface 400 may be a visual representation that is associated with the stained cells. In the present example, the target cells may be stained with a first light-responsive dye that facilitates the tracking of a live cell count, and a second light-responsive dye that facilitates the tracking of the dead cell count. The user interface 400 may allow for visualization of the presence of the first light-responsive dye for live cell tracking and the presence of the second light-responsive dye for dead cell tracking.

As shown in FIG. 4, the user interface 400 includes a display region 402. The display region 402 may represent at least a portion of cells from the operation 212. For example, the display region 402 may be indicative of a portion of the dissociated cells that is analyzed in order to facilitate counting of live and dead cells. Accordingly, for purposes of illustration, the display region 402 is shown including live cells 406 and dead cells 410. The live cells 406 may be those having or otherwise associated with the first color, and the dead cells 410 may be those having or otherwise associated with the second color. The live cells 406 and the dead cells 410 are represented in the display region 402 based on a magnification 414, which may be modifiable by a user or computer-implemented technique.

The representative first color and second color of the live cells 406 and the dead cells 410, respectively, may allow for the determination of analysis of various properties of the cells. As one example, the differing colored live cells 406 and dead cells 410 may allow for a quantity of cells per unit volume to be counted or determined. The quantity of per unit volume of live cells 406 and the quantity of per unit volume dead cells 410 may be compared in order to determine a relative concentration of living cells to dead cells. In the example of FIG. 4, the display region 402 may be overlaid or associated with a control panel 452. The control panel 452 may display the current determination of a living cell concentration 456 versus a dead cell concentration 470. For example, a determination of the concentration of live cells 406 relative to the dead cells 410 may result in the living cell concentration 456 having a value of 90% and the dead cell concentration 470 having a value of 10%. It will be appreciated that the user interface 400 shows information associated with how many cells were isolated from the patient tumor sample.

Figure 5:
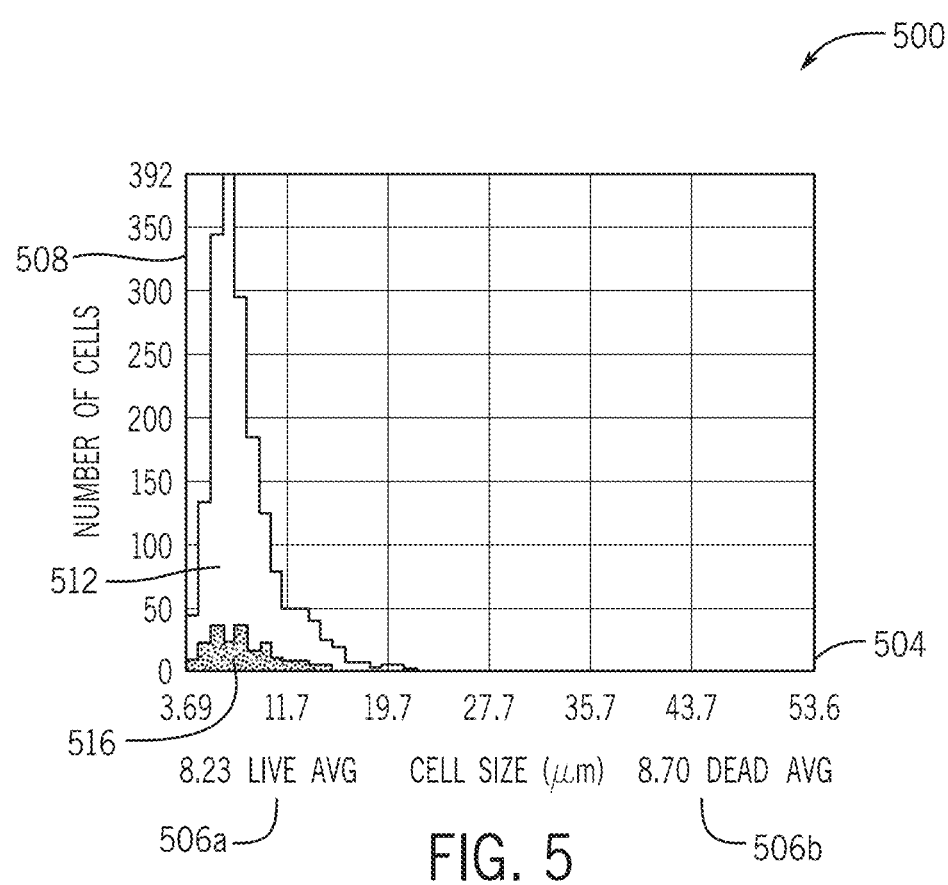
FIG. 5 depicts a chart showing the relative concentration and size distribution of living cells and dead cells.

For example, and with reference to FIG. 5 a chart 500 is depicted including additional information corresponding to the living cells 406 and the dead cells 410 shown in FIG. 4. For example, the chart 500 may show a relative concentration or number of living/dead cells with respect to cell size. As shown in FIG. 5, the chart 500 includes a cell size axis 504, a cell quantity axis 508, a live cell distribution 512, a dead cell distribution 516, live cell size average 506a, dead cell size average 506b. The cell size axis 504 may be representative of an approximate size of a given target cell. In FIG. 5, the size is represented in micrometers; however, other appropriate units may also be used. The cell quantity axis 508 may include a count of the number of cells for a given sample or portion thereof measured.

The live cell distribution 512 and the dead cell distribution 516 may be representative of a quantity of cells for a respective cell size. In some cases, the distributions 512, 516 may be a histogram or other representation in which a quantity of cells are depicted for a given range of cell sizes. The live cell average 506a may represent an average size of the live cells represented by the live cell distribution 512. The dead cell average 506b may represent an average size of the dead cells represented by the dead cell distribution 516.

Figure 6:
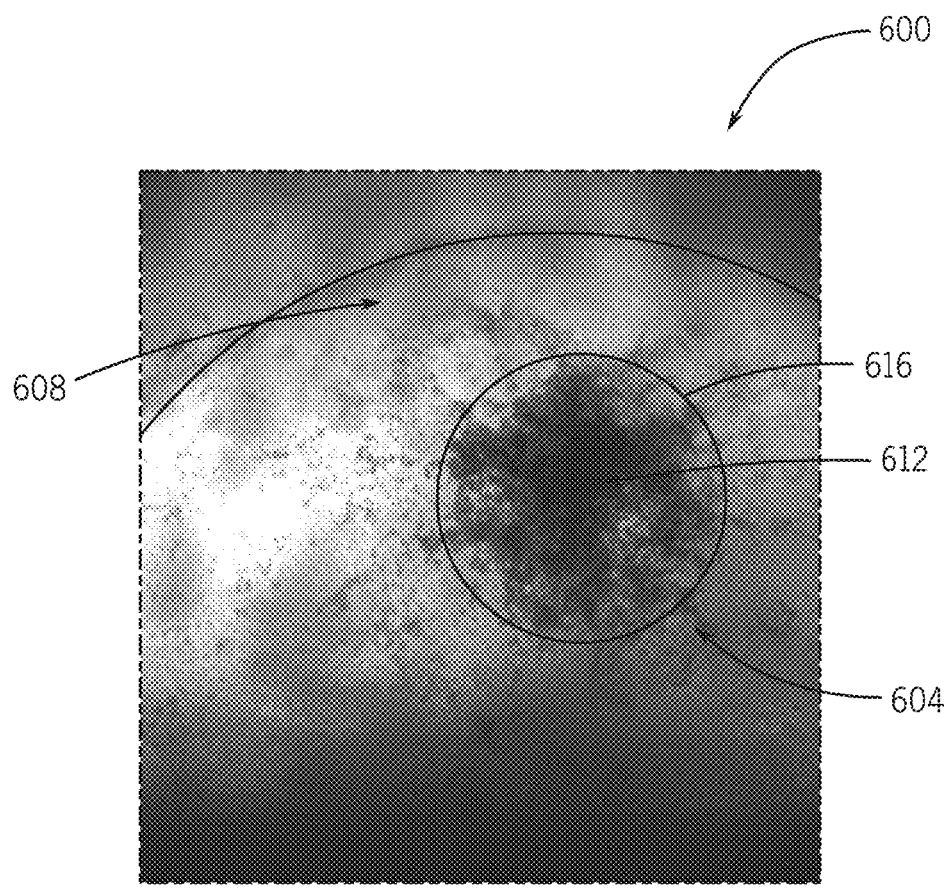
FIG. 6 depicts a 2D micrograph of an example spheroid.

With reference to FIG. 6, an example culture 600 is depicted. The culture 600 may represent a solid cell culture formed via the optional spheroid formation operation 216 and hydrogel embedding operation 220, described above with respect to FIG. 2. For example, the culture 600 is shown in FIG. 6 as including a hydrogel 608. The hydrogel 608 may contain hyaluronic acid and collagen to mimic core components of human tissue extracellular matrices and disease-specific cell niches, like those found in breast tumors. The hydrogel 608 is shown encapsulating a spheroid 604. The spheroid 604 may include target cells 612, such as any of the cells described herein. The target cells 612 may be stained with a light-responsive dye.

The arrangement of the cell culture including the spheroid 604 may facilitate the tracking of tumor properties over time. As one example, a representative circumference 616 is shown in FIG. 6. The representative circumference 616 may correspond to a size value for the spheroid 604 or other cell or portion of the culture 600. The culture 600 may be exposed to treatment agents as described herein. Subsequently, a size of the circumference 616 or other property of the culture 600 may be measured in order to determine a change over time. The change may be indicative of a treatment efficacy for the treatment agent when compared against the control/baseline. As one example, a decrease in a size of the circumference 616 may provide information to a clinician regarding the efficacy of a treatment that was administered to the cell culture 600.

The solid cell culture 600 may be stained with one or more of the light-responsive dyes described herein. Properties of the solid cell culture 600 and spheroid 604 may therefore be measured using the light-responsive dyes. As an illustration, with reference to FIGS. 7A-7C, representations of a solid cell culture 700 are shown under different conditions for analyzing the components of the cell culture. The example of FIGS. 7A-7C shows a spheroid of an ovarian tumor for purposes of illustrations, in other cases, other tumors may be represented using similar techniques. With reference to FIG. 7A, the cell culture 700 is shown in a condition in which a live cell dye causes a representation 704 to be illuminated or represented. The representation 704 may be indicative of the physical properties of live cells, including cell position and size. With reference to FIG. 7B, the cell culture 700 is shown in a condition in which a dead cell dye causes a representation 708 to be illuminated or represented. The representation 708 may be indicative of the physical properties of dead cells, including cell position and size. In some circumstances, it may be beneficial to overlay the representation 704, 708, for example, to more accurately track cells as the cells transition from living to dead. With reference to FIG. 7C, the cell culture 700 is shown in which the representations 704, 708 are overlaid to define a representation 712. The representation 712 may be a composite visual representation of the living cell and the dead cell dye. The representations 704, 708, 712 may change over time, such as changing in response to administration of one or more treatment agents. The change in representation 704, 708, 712 as explained herein, may be analyzed to determine a treatment efficacy.

With reference to FIGS. 8A and 8B, a microfluidic chip 800 is disclosed. The microfluidic chip 800 may be used in conjunction with the operation 224 of setting the hydrogel in a chip, as described above with reference to FIG. 2. The microfluidic chip 800 may be configured to mimic an environment of a human organ. For example, the microfluidic chip 800 may be configured to replicate an environment of a human organ in order to establish an environment where cells can live ex vivo for a period of time. In this regard, the microfluidic chip 800 may include a compartment or cell culture chamber to hold cells, such as any of cells or cell cultures described herein. The microfluidic chip 800 may include layers to cover or shield the cell cultures to block contaminants from the cell culture while also allowing gas, such as oxygen to reach the cell culture. The microfluidic chip 800 may also be configured to circulate growth media and treatment agents to the solid cell culture held therein. The growth media may allow the cells to survive for a period of time, ex vivo.

The microfluidic chip 800 may be a multilayered structure. FIG. 8A shows an exploded view of a stack up of layers and components that may be used to form the microfluidic chip 800. Each component layer of FIG. 8A is shown in a top view. With reference to FIG. 8A, a base layer 802, a first body portion layer 812, a second body portion layer 822, a third body portion layer 832, a coupling portion 842, and a gas permeable layer 852 is shown. In other examples, the microfluidic chip 800 may include more or fewer layers, such as including one or more sterilization layers, films, adhesives, and so on that may be used to prepare the microfluidic chip 800 for dosing. The microfluidic chip 800 may also be associated with one or more flow restrictors 880 (FIG. 8C). In the example of FIG. 8A, the base layer 802 may be a substantially solid section of the chip 800 upon which the other layers of the chip 800 are arranged. The base layer 802 may have a size corresponding to a size of a standard microscope slide to foster compatibility.

The first body portion layer 812, the second body portion layer 822, and the third body portion layer 832 may be layers of a body 801 that define a channel 862, a first volume 864 (including a first cell culture chamber 814) and a second volume 866 (including a second cell culture chamber 816) of the chip 800. For example, the first body portion layer 812 may define a first cell culture chamber 814 and a second cell culture chamber 816, which may each be defined by openings or through portions through the first body layer 812. The second body portion layer 822 may define a second body portion first hole 824 and a second body portion second hole 826, which may each define openings or through portions through the second body layer 822. Further, the third body portion layer 832 may define a third body portion first hole 834 and a third body portion second hole 836, which may each define openings or through portions through the third body layer 832.

As shown in cross-section view of FIG. 8A, the first body portion layer 812, the second body portion layer 822, and the third body portion layer 832 may be stacked relative to one another such that the first cell culture chamber 814, second body portion first hole 824, and third body portion first hole 834 cooperate to define a first volume 864. The first volume 864, including the first cell culture chamber 814, may have a substantially cylindrical shape with a closed bottom end and an open top end. In one example, the first cell culture chamber 814 may have a diameter of preferably about 6.75 mm. In other cases, the diameter may be more or less than 6.75 mm such as being less than about 5 mm, less than about 3 mm and/or other appropriate value for a given application. Further, the first body portion layer 812, the second body portion layer 822, and the third body portion layer 832 may be stacked relative to one another such that the second cell culture chamber 816, second body portion second hole 826, and third body portion second hole 836 cooperate to define the second volume 866. The second volume 866, including the second cell culture chamber 816, may have a diamond or rectangular shape with a closed bottom end and an open top end.

The body 801 may also define the channel 862. For example, and as shown in FIG. 8A, the second body portion layer 822 includes an elongated through portion 828. The elongated through portion 828 may extend through a complete thickness of the second body portion layer 822 and through a portion of the second body portion first opening 824 and the second body portion second opening 826. The first body portion layer 812, the second body portion layer 822, and the third body portion layer 832 may be stacked relative to one another such that the first body portion layer 812 and the third body portion layer 832 close the bottom and the top of the elongated through portion 828, respectively, in order to define the channel 862.

The elongated through portion 828 may extend between opposing ends of the second body portion layer 822. The third body portion layer 832 may cover the elongated through portion 828 and define a first lumen 833a and a second lumen 833b, each extending into the elongated through portion 828. For example, the first lumen 833a may extend through a thickness of the third body portion layer 832 at a first end and into the elongated through portion 828. The second lumen 833b may extend through the thickness of the third body portion layer 832 at a second, opposing end and into the elongated through portion 828. The first and second lumens 833a, 833b may extend into the elongated through portion 828 in order to facilitate a fluidic coupling of the channel 862 to a fluid circuit.

For example, and as shown in FIG. 8A, the coupling portion 842 may include an inlet feature 843a and an outlet feature 843b. As shown in FIG. 8B, the inlet feature 843a and the outlet feature 843b may be barbs that protrude from a topmost surface of the microfluidic chip 800. The inlet feature 843a may be alignable with or receivable by the first lumen 833a and configured to define a fluid connection between a tubing of a circulation system and the channel 862. The outlet feature 843b may be alignable with or receivable by the second lumen 833b and configured to define a fluid connection between additional tubing of the circulation system and another end of the channel 862. As described herein, this configuration may allow the chip 800 to be fluidly coupled to a circulation system in which treatment agents are circulated through the chip 800 alongside growth media. For example, fluid or media of a variety of purposes may be introduced to the chip 800 via inlet feature 843a and caused to flow through the chip 800 via the first lumen 833a, the channel 862, the second lumen 833b, and exiting via the outlet feature 843b.

With further reference to FIG. 8A, the gas permeable layer 852 may include a membrane, film, or other layer configured to shield and cover the first and second volumes 864, 866, containing the first and second cell culture chambers 814, 816. The gas permeable layer 852 may be configured to shield or cover the volumes 864, 866 while allowing gas, such as oxygen, ingress and egress between the cell culture chambers 814, 816 and an external environment. In this manner, cell cultures held therein may be exposed to an oxygen rich environment and/or an oxygen poor environment as needed based on a particular application. The third body portion layer 832 is shown as including an adhesive surface 835. The gas permeable layer 852 may be attachable to the body via the adhesive surface 835 subsequent to loading the chip 800 with a cell culture, as described herein.

With reference to the cross-sectional view of FIG. 8B, the chip 800 may be coupled such that the base layer 802, the first body portion layer 812, the second body portion layer 822, the third body portion layer 832, the coupling portion 842, and the gas permeable layer 852 are stacked relative to one another. In the assembled configuration, the channel 862 is shown extending through the body 801 between the first lumen 833a and the second lumen 833b. The first lumen 833a is fluidly coupled to the inlet feature 843a. The second lumen 833b is fluidly coupled to the outlet feature 843b. As shown in FIG. 8B, the inlet feature 843a may be fluidly coupled with a first tube 906a, and the outlet feature 843b may be fluidly coupled with a second tube 906b. The first and second tubes 906a, 906b may be portions of tubing of a circulation system (e.g., such as that provided by the microfluidic device 1000 of FIGS. 10 and 11). The tubes 906a, 906b may be inserted or received by the respective inlet feature 843a and outlet feature 843b. The inlet and outlet features 843a, 843b may be configured to define a sealed connection with the respective tubes 906a, 906b.

As shown in FIG. 8B, the chip 800 may be configured to define a segment of a flow path for the circulation system. For example, the first tube 906a may introduce an inlet flow $F_i$ into the chip 800 at the inlet feature 843a. The inlet flow $F_i$ may be a flow of a media including treatment agents. The flow of the media and/or treatment agents and/or other agents may progress to the channel 862 defined by the body 801. The channel 862 may run adjacent to both the first cell culture chamber 814 and the second cell culture chamber 816. In this regard, the flow of media and/or treatment agents continue through the channel 862 and alongside and/or into a portion of the first cell culture chamber 814 and/or the second cell culture chamber 816. As described herein, one or both of the first cell culture chamber 814 and/or the second cell culture chamber 816 may include cells encapsulated in a hydrogel, such as any of the arrangements of cells and hydrogels described herein. The channel 862 may therefore be configured to route the growth media and/or treatment agents for interaction with the cells/hydrogel included in the respective cell culture chambers 814, 816. For example, a solid cell culture (including cells and hydrogel) may be deposited into the first cell culture chamber 814 and/or the second cell culture chamber 816. The growth media may be circulated through the chip 800, such as along the channel 862 in order to flow over the cells and hydrogel held therein. An exposed solid cell culture may therefore be defined in the chip once the solid cell culture is put in the chip and the growth media is circulated therethrough. The interaction of the media and/or the treatment agents with the cells may cause the cells to retain at least a portion of the media and/or treatment agents in the cell culture chamber. The flow may continue along the channel 862 and exit the chip at the outlet feature 843b at a flow $F_o$.

FIG. 8C is a cross-section view of a flow restrictor 880 for use with the microfluidic chip 800 in a fluid circuit. The flow restrictor 880 may be implemented in order to facilitate sterility in the system, such as by preventing contamination of the chip 800 and cells therein. The flow restrictor 880 may therefore include one or more filter elements. The flow restrictor 880 may therefore further include one or more reductions or changes in a diameter in the flow path in order to increase or modify a pressure gradient of the flow across the restrictor 880, among other uses.

In the example of FIG. 8C, the flow restrictor 880 is shown including a first straight barb 882. The first straight barb 882 defines a first barb channel 883 therethrough. The flow restrictor 880 may generally be arranged adjacent the inlet or outlet of the microfluidic chip 800. In this regard, the first straight barb 882 may be fluidly coupled to one of the inlet or outlet features 843a, 843b. For example, the flow restrictor 880 may be fluidly coupled to tubing that is received by the first straight barb 882 and one of the barbs of the inlet or outlet features 843a, 843b to complete the fluidic coupling. The flow restrictor 880 shown in FIG. 8C also includes a second straight barb 896 that defines a second barb channel 897. The second straight barb 896 may be substantially analogous to the first straight barb 882. The second straight barb 896 may be fluidly coupleable with a component of the microfluidic device (e.g., the microfluidic device 1000 of FIG. 10) via tubing and/or other connector. Multiple flow restrictors can be used. As one example, a first flow restrictor can be used at an inlet of a given microfluidic chip and a second flow restrictor can be used at an outlet of the microfluidic chip.

The flow restrictor 880 may include multiple layers arranged generally between the first and second straight barbs 882, 896 to facilitate the foregoing functionalities. For example, the flow restrictor 880 is shown including a first layer 884 and a first hole 885, and an adjacent second layer 886 and a second hole 887. The first straight barb 882 may be at least partially received by the first hole 885. The second hole 887 may generally be aligned with the first hole 885. The second hole 887 has a diameter that is less than a diameter of the first hole 885. In this regard, the first barb channel 883, the first hole 885 and the second hole 887 may define a flow path with the second hole 887 operating to reduce or restrict the flow through the flow restrictor 880. The flow restrictor 880 is further shown as including a filter layer 888 with a filter hole 889 generally adjacent the second hole 887. The filter layer 888 may house or hold a filter 890 in the filter hole 889. Multiple constructions of the filter 890 are possible. In one example, the filter 890 may include a glass microfiber filter. In some cases, multiple separate filters may be used.

Adjacent the filter layer 888, the flow restrictor 880 is shown as including a third layer 892 and third hole 893, and an adjacent fourth layer 894 and fourth hole 895. The third layer 892 and third hole 893, and the fourth layer 894 and fourth hole 895 may generally mirror the first layer 884 and first hole 885, and second layer 886 and second hole 887. In this regard, the third hole 893 may be generally smaller in diameter than the fourth hole 895. The second straight barb 896 may be at least partially received by the fourth hole 895.

FIGS. 9A-9E depict an operation of loading the microfluidic chip 800 with a cell culture.

Figure 9C:
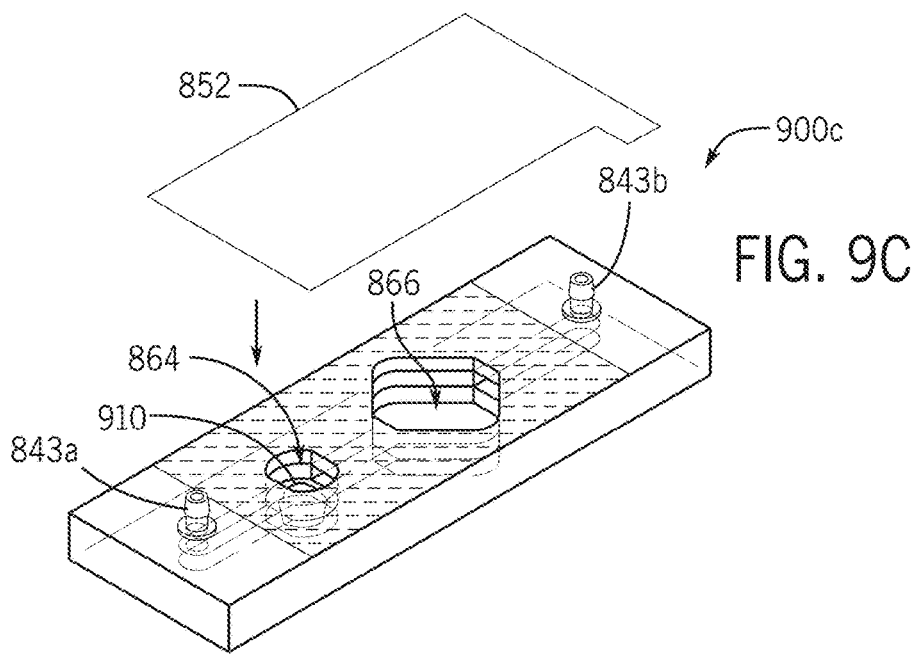
FIG. 9C depicts another operation of the microfluidic chip of FIG. 8A.
Figure 9D:
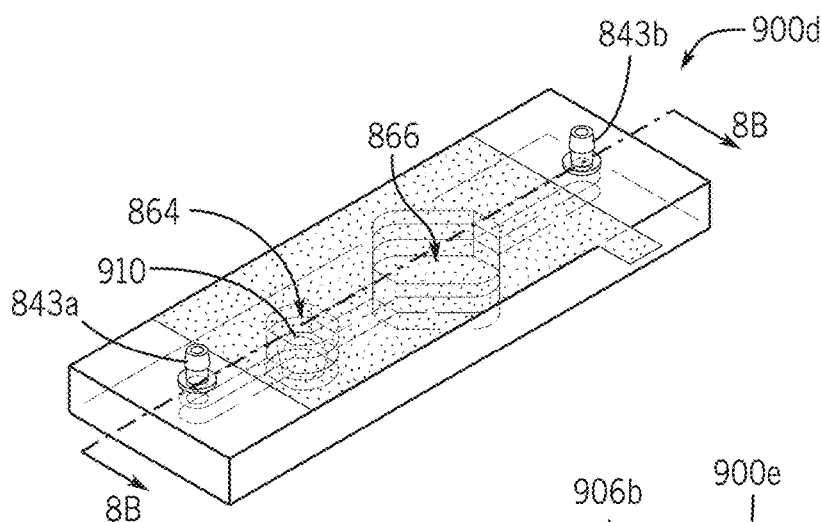
FIG. 9D depicts another operation of the microfluidic chip of FIG. 8A.
Figure 9E:
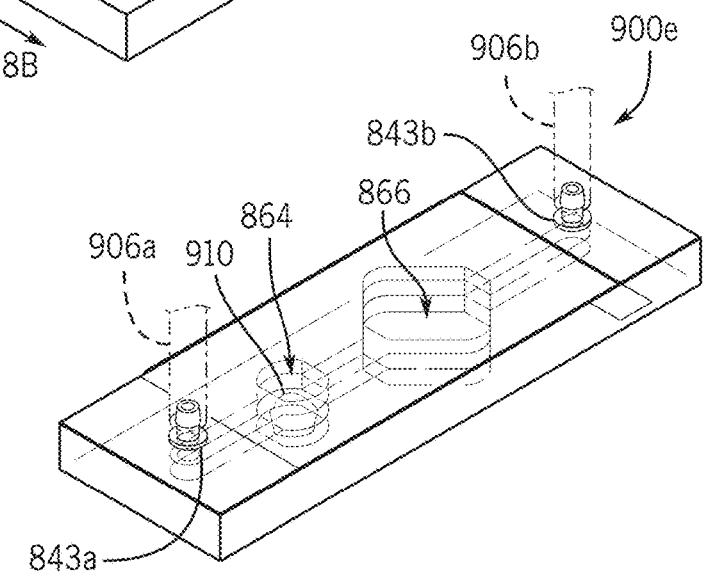
FIG. 9E depicts another operation of the microfluidic chip of FIG. 8A.

With reference to FIG. 9A, an operation 900a is shown in which the first cell culture chamber 814 of the first volume 864 is loaded with a solid cell culture (e.g., any combination of cells and hydrogel described herein). For example, a pipet 902 or other instrument may selectively introduce a solid cell culture 910 into the first cell culture chamber 814. In some cases, the second cell culture chamber 816 of the second volume 866 may also be loaded with a solid cell culture. With reference to FIG. 9B, an operation 900b is shown in which an adhesive backing 879 is removed to reveal the adhesive surface 835 of the body 801. The adhesive backing 879 may reveal the adhesive surface 835 in order to prepare the body 801 for attachment with the gas permeable layer 852. For example, and with reference to FIG. 9C, an operation 900c is shown in which the gas permeable layer 852 may be positioned over the body 801. In some cases, the gas permeable layer 852 may cover the top of both the first and second volumes 864, 866, containing the first cell culture chamber 814 and the second cell culture chamber 816, as shown in FIG. 9D at operation 900d. The gas permeable layer 852 may be attached to the body 801 via the adhesive surface 835. With reference to FIG. 9E, an operation 900e is shown in which the first tube 906a is fluidly coupled with the inlet feature or barb 843a and the second tube 906b is fluidly coupled with the outlet feature or barb 843b.

Figure 10:
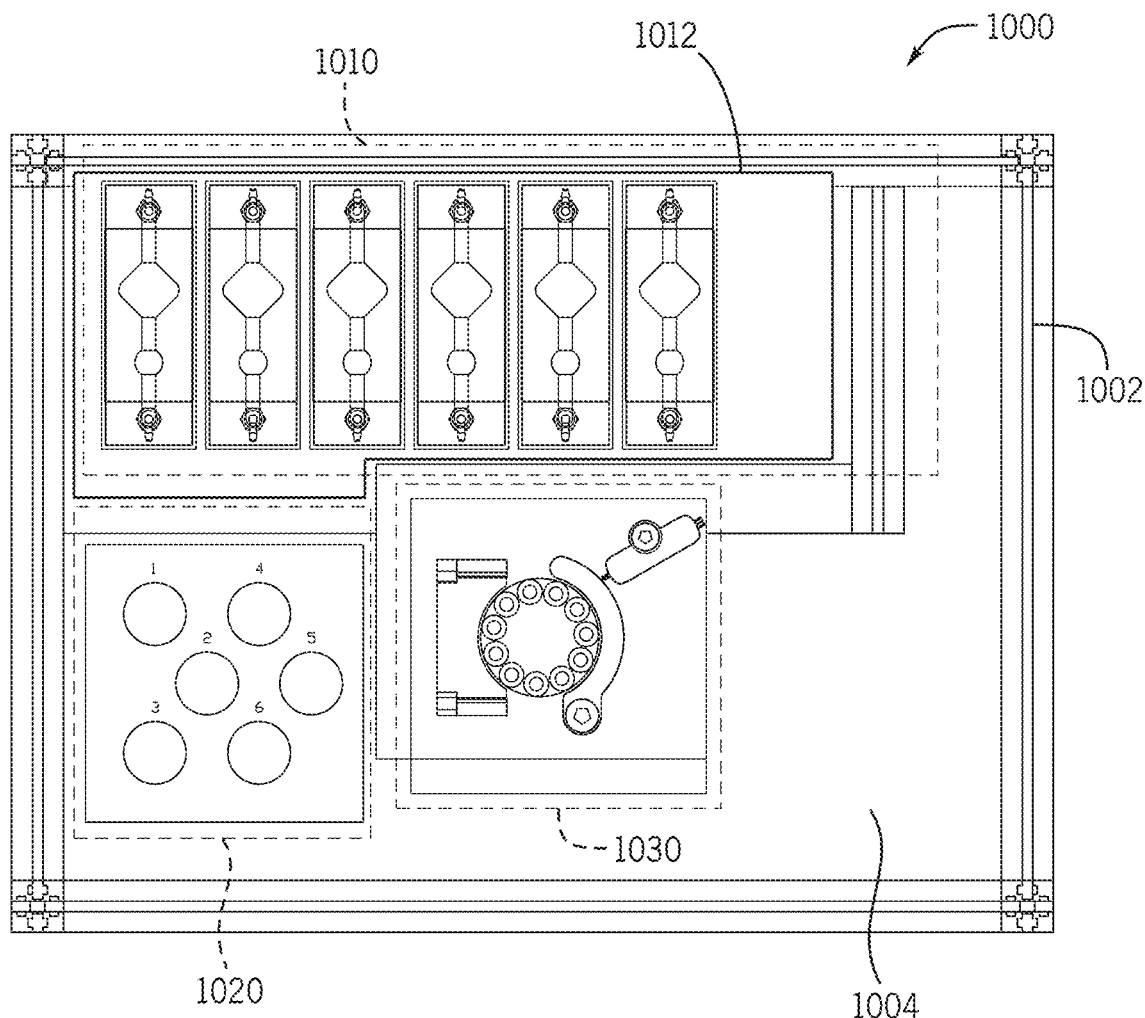
FIG. 10 depicts a top schematic view of a microfluidic device for use with the microfluidic chip of FIG. 8A.
Figure 11:
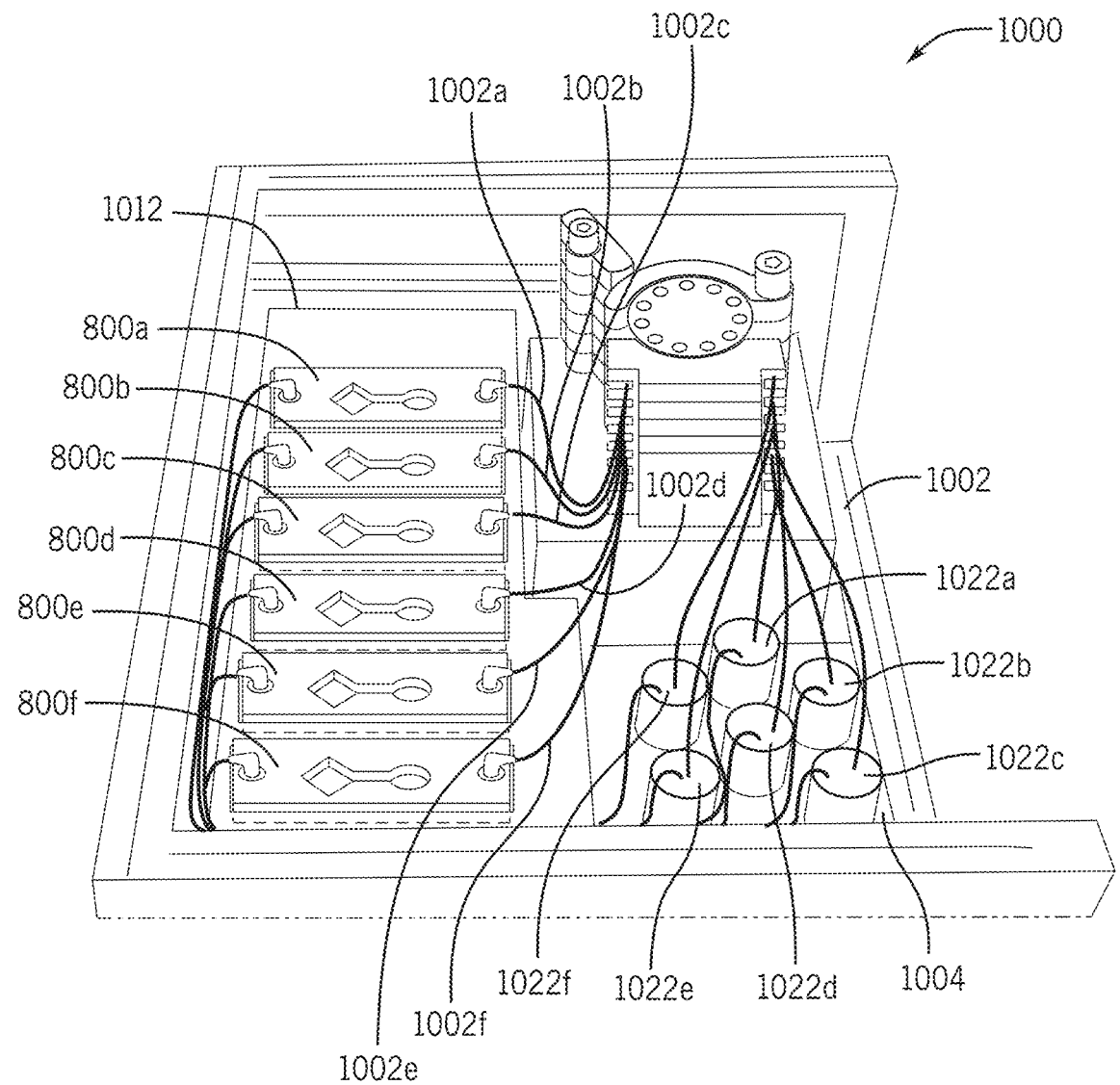
FIG. 11 depicts an isometric view of the microfluidic device performing a dosing operation.

With reference to FIGS. 10 and 11, a microfluidic device 1000 is shown. The microfluidic device 1000 may be configured to implement the operation 232 of FIG. 2, in which the solid cell culture (e.g., the cells and hydrogel desired herein) is exposed to treatment agents. Broadly, the microfluidic device 1000 may be configured to provide treatment agents alongside growth media to multiple microfluidic chips, in parallel. The microfluidic device 1000 may define closed circuits for each chip that are generally fluidly isolated and separated from the circuits of the other chips. The microfluidic device 1000 may be configured to provide different treatment agents, growth media, or other solutions to the chips, so that a response of the solid cell cultures may be determined over time.

To facilitate the foregoing, the microfluidic device 1000 may include a housing 1002, a platform 1004, a staging section 1010, a dosing bank 1020, and a pump 1030. The housing 1002 may provide a structural platform for the various components of the microfluidic device 1000, including the pump 1030 and the dosing bank 1020. The housing 1002 may also provide a structure upon which to arrange and temporarily store chips during dosing. The housing 1002 may have one or more open sides, as shown in FIG. 11. In other cases, the housing 1002 may enclose one or more components of the microfluidic device 1000. In yet other cases, the housing 1002 may be omitted entirely.

The staging section 1010 may be configured to arrange a plurality of microfluidic chips in the microfluidic device 1000. The staging section 1010 may be a portion of the housing 1002. In other cases, the staging section 1010 may include a raised platform, slots, or other features for receiving and securing chips in a particular position in the staging section 1010. In some cases, and as shown in the example of FIGS. 10 and 11, the staging section 1010 may include a chip tray 1012. The chip tray 1012 is shown as holding six microfluidic chips: a first microfluidic chip 800a, a second microfluidic chip 800b, a third microfluidic chip 800c, a fourth microfluidic chip 800d, a fifth microfluidic chip 800e, and a sixth microfluidic chip 800f. Each of chips 800a-800f may be substantially analogous to the microfluidic chip 800 described above with respect to FIGS. 8A-9E; redundant explanation of which is omitted for clarity. While various configurations are possible, the chip tray 1012 may include a recess or groove that is configured to accommodate a single chip. For example, a given chip may be received in the groove such that at least side to side movement of the chip is mitigated on the tray 1012. While the examples of FIGS. 10 and 11 show the chip tray 1012 as including a grooves for six chips, other configurations are possible, including trays that hold more or fewer chips.

The dosing bank 1020 may include a plurality of reservoirs. The dosing bank 1020 may include a plurality of reservoirs corresponding to the plurality of chips arranged at the staging section 1010. For example, and as shown in FIG. 11, the dosing bank may include a first reservoir 1022a, a second reservoir 1022b, a third reservoir 1022c, a fourth reservoir 1022d, a fifth reservoir 1022e, and a sixth reservoir 1022f. The reservoirs 1022a-1022f may be configured to hold a media, such as any of the growth media described herein. The reservoirs 1022a-1022f may further be configured to hold treatment agents, or substantially any other fluid for introduction to respective ones of the chips 800a-800f. The reservoirs 1022a-1022f may be exposed or exposable such that additional media and/or treatment agents may be added over time. The reservoirs 1022a-1022f may also be associated optionally with covers to shield the media held therein from contaminants during dosing. For example, one or more or all of the reservoirs 1022a-1022f may include a cap, such as an aluminum cap, to hermetically seal the respective reservoir 1022a-1022f.

The pump 1030 may be configured to complete a fluid circuit between respective ones of the chips 800a-800f and the reservoirs 1022a-1022f. The pump 1030 may be a peristaltic pump, pneumatic pump and/or any other appropriate pump or pumping device. The pump 1030 may be configured to define separate fluid circuits between a given one of the chips 800a-800f and the reservoirs 1022a-1022f. For example, the pump 1030 may be configured to cause circulation of fluid between respective ones of the reservoirs 1022a-1022f and the chips 800a-800f without fluid of one of the reservoirs crossing over or contaminating another reservoir. This may allow each chip to be dosed separately such that a reading or measurement of each chip may be taken in order to determine the impact from a particular solution held in the corresponding reservoir. While the pump 1030 is shown as a single assembly, in other cases, the pump 1030 may represent multiple pumps. Further, the pump 1030 is shown as including six circulation paths. In other cases, the pump 1030 may define more or fewer paths.

In the example of FIG. 11, the pump 1030, the chips 800a-800f, and the reservoirs 1022a-1022f are coupled to one another to define six circulation paths. For example, the pump 1030, the first microfluidic chip 800a, and the first reservoir 1022a are coupled to one another to define a first fluid circulation path 1002a. Further, the pump 1030, the second microfluidic chip 800b, and the second reservoir 1022b are coupled to one another to define a second fluid circulation path 1002b. Further, the pump 1030, the third microfluidic chip 800c, and the third reservoir 1022c are coupled to one another to define a third fluid circulation path 1002c. Further, the pump 1030, the fourth microfluidic chip 800d, and the fourth reservoir 1022d are coupled to one another to define a fourth fluid circulation path 1002d. Further, the pump 1030, the fifth microfluidic chip 800e, and the fifth reservoir 1022e are coupled to one another to define a fifth fluid circulation path 1002e. Further, the pump 1030, the sixth microfluidic chip 800f, and the sixth reservoir 1022f are coupled to one another to define a sixth fluid circulation path 1002f. The circulation paths 1002a-1002f may be separate fluid paths that are fluidly isolated from one another. The pump 1030 may cause a circulation along circulation paths 1002a-1002f independent from one another. For example, the pump 1030 may cause media, treatment agents and the like to circulate along the first circulation path between the first reservoir 1022a and the first chip 800a, the second reservoir 1022b and the second chip 800b, the third reservoir 1022c and the third chip 800c, the fourth reservoir 1022d and the fourth chip 800d, the fifth reservoir 1022e and the fifth chip 800e, and the sixth reservoir 1022f and the sixth chip 800f.

The chips 800a-800f may be removed individually from the microfluidic device 1000. For example, individual ones of the chips 800a-800f may be removed from the microfluidic device 1000 for imagining and analysis. As described above with respect to FIG. 2, an individual chip may be removed and imaged using fluorescence microscopy or other techniques in which properties of the solid cell culture are determined for a single point in time, including, but not limited to, cell culture size color, position, and density. Subsequent to the imaging, the chip may be recoupled to the microfluidic device 1000. The microfluidic device 1000 may proceed to provide additional treatment agents, media, and so one to the respective microfluidic chip. The chip may be removed again from the microfluidic device 1000 in order to conduct further imaging of the solid cell culture for a second, later point in time. For example, the cell culture color, size, position, and density can be detected at the second point in time and/or a variety of other cell characteristics. The characteristics of the solid cell culture at the second point in time can be compared with the characteristics of the solid cell culture at the first point in time to determine other characteristics, including cell migration distance, cell migration speed, maximum migration vector, maximum migration speed, and so on, as described herein. The chip may be removed repeatedly, such as a third, fourth, fifth, or more times in order to conduct further imaging of the solid cell culture for a third, fourth, fifth, or more later points in time.

Figure 12:
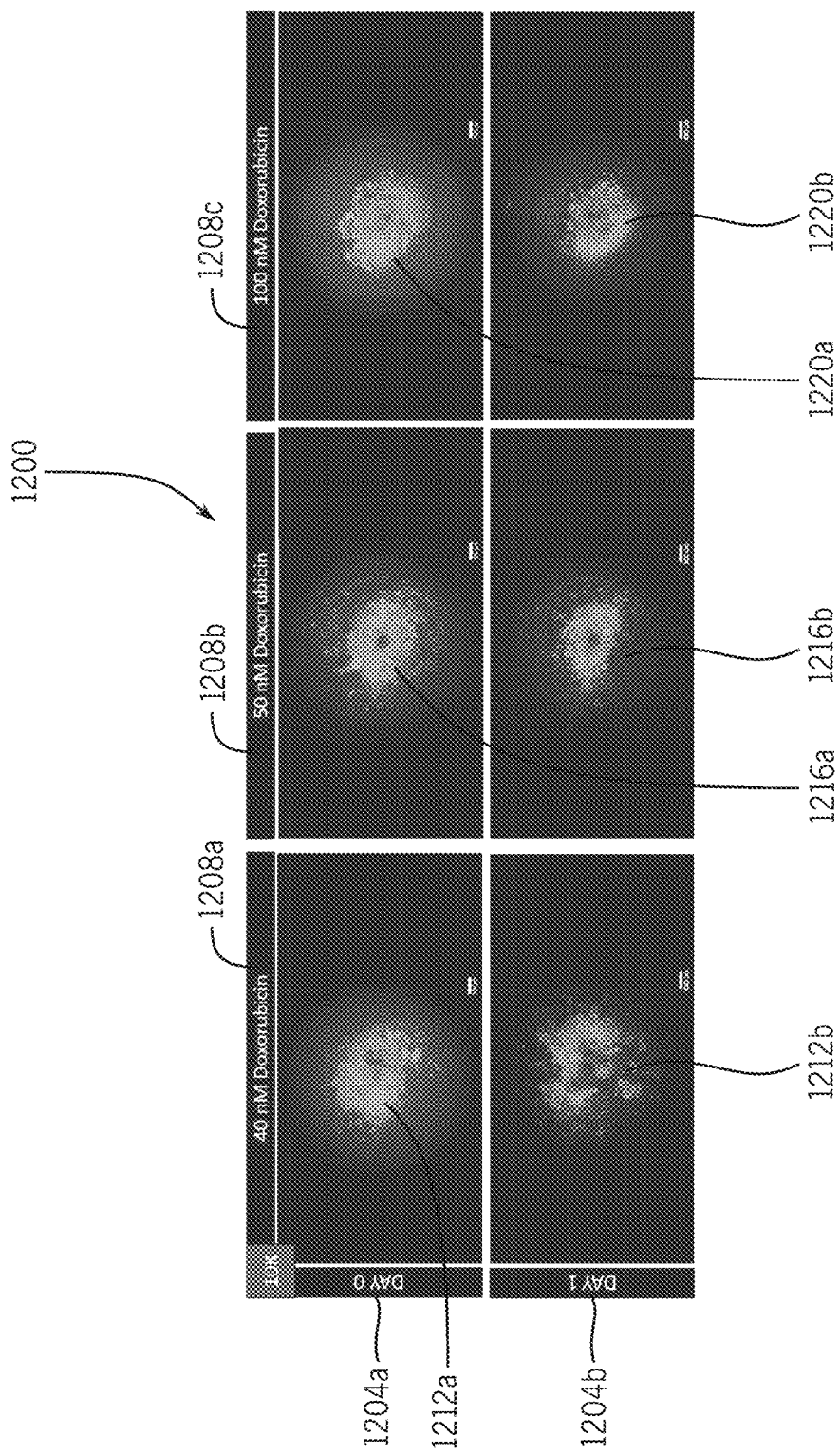
FIG. 12 depicts an example spheroid of isolated and dyed tumor cells after a dosing operation.

In one example, the width or diameter of a spheroid is measured and compared at different time points. Single cells surrounding the spheroid are tracked individually or in clusters. Movement of single cells can be tracked to determine if the cells are entering or exiting the spheroid. The change in spheroid size and/or the behavior of single cells can be used individually or together to predict a patient response to a given treatment. FIG. 12 shows an example report 1200 including images of representative cell cultures after a period of dosing. A spheroid exposed to a treatment that stays stable or grows may indicate a poor response, while a spheroid that shrinks may indicate a good response. In this regard, the given image or other representation of a cell culture may be compared with an image of the culture prior to dosing in order to determine a change in size of the spheroid.

With reference to FIG. 12, the example report 1200 includes a first cell culture column 1208a, a second cell culture column 1208b, and a third cell culture column 1208c. In one example, each of columns 1208a-1208c may be indicative of a different cell culture held by a different microfluidic chip (e.g., one of the microfluidic chips 800a-800f of FIGS. 10 and 11). Each of the cell cultures in the respective chips may be dosed with a different treatment agent, different strength or concentration of treatment agent, and/or no treatment agent in order to evaluate the response of the cell culture to a variety of conditions over time (e.g., as may be depicted in various three-dimensional images, as shown herein with respect to FIG. 16). In the example of FIG. 12, the first cell culture column 1208a corresponds to a cell culture for administration of a first treatment agent at a first dose (e.g., 40 nM doxorubicin), the second cell culture column 1208b corresponds to a cell culture for administration of a second treatment agent at a second dose (e.g., 50 nM doxorubicin), and the third cell culture column 1208c corresponds to a cell culture for administration of a third treatment agent at a third dose (e.g., 100 nM doxorubicin). It will be appreciated that the particular treatment agents and doses are presented for purposes of illustration only, and that substantially any other treatment agent and dose may be used as appropriate for evaluating treatment efficacy.

In this regard, the report 1200 includes a first time point row 1204a, and a subsequent time point row 1204b. In the example of FIG. 12, the first time point row 1204a may correspond to a period of time before dosing, such as at day zero. The subsequent time point row 1204b may correspond to a later time point after some period of dosing. As shown in FIG. 12, the subsequent time point row 1204b may be after one day of dosing. In other cases, the subsequent time point row 1204b may correspond to another period of dosing, such as after two days, three days, four days, five day, and so on. The cell cultures may be evaluated at each of the time points (and other time points) in order to evaluate treatment efficacy. For example, the cell culture associated with the first cell culture column 1208a may be imaged, according to any of the techniques described herein, at a time associated with the first time point row 1204a (e.g., a time prior to dosing) in order to produce a first representation 1212a of the cell culture. The cell culture associated with the first cell culture column 1208a may subsequently be dosed (e.g., with 40 nM doxorubicin) and imaged at a time associated with the second time point row 1204b (e.g., after one day or so of dosing) in order to produce a second representation 1212b of the cell culture. Further, the cell culture associated with the second cell culture column 1208b may be imaged, according to any of the techniques described herein, at a time associated with the first time point row 1204a (e.g., a time prior to dosing) in order to produce a first representation 1216a of the cell culture. The cell culture associated with the second cell culture column 1208b may subsequently be dosed (e.g., with 50 nM doxorubicin) and imaged at a time associated with the second time point row 1204b (e.g., after one day or so of dosing) in order to produce a second representation 1216b of the cell culture. Further, the cell culture associated with the third cell culture column 1208c may be imaged, according to any of the techniques described herein, at a time associated with the first time point row 1204a (e.g., a time prior to dosing) in order to produce a first representation 1220a of the cell culture. The cell culture associated with the third cell culture column 1208c may subsequently be dosed (e.g., with 100 nM doxorubicin) and imaged at a time associated with the second time point row 1204b (e.g., after one day or so of dosing) in order to produce a second representation 1220b of the cell culture. The respective second representations 1212b, 1216b, 1220b may be evaluated using the computer vision tools described herein, including producing various charts, reports, graphs and so on, as described below in relation to FIGS. 13A-17.

Figure 13A:
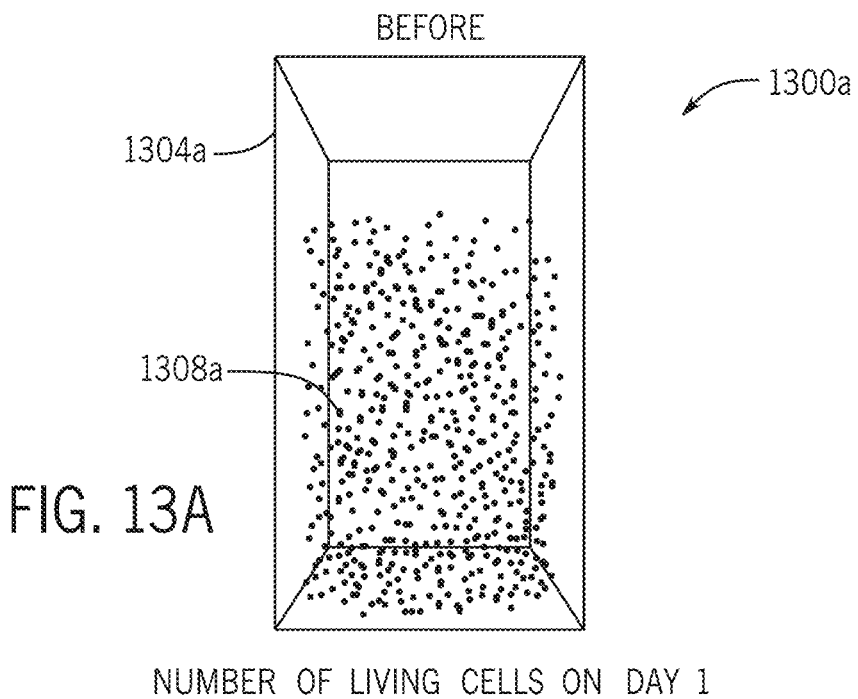
FIG. 13A depicts a chart showing a first quantity of cells at a first time point.

In this regard, with reference to FIGS. 13A-17, various charts, reports, and graphs are depicted that are representative of the imaging and analyzing operations of the computer vision system described above with reference to FIG. 2. It will be appreciated that the following charts, reports, and graphs are depicted as examples. In other cases, additional or alternative charts, reports, and graphs may be used. For example, and with reference to FIG. 13A, a chart 1300a is shown including a grid 1304a and a first representation 1308a. The grid 1304a may be a three-dimensional image representative of a three-dimensional space associated with the solid cell culture. The first representation 1308a may be representative of a three-dimensional position of particular items of interest, such as living cells in a three-dimensional space. The chart 1300a may be produced, in one example, via two-dimensional images captured of the solid cell culture, in which the size and location of cells of interest are determined using the light-responsive dye. The two-dimensional images may be stitched together in order to produce a three-dimensional image. In this regard, the first representation 1308a may represent a composite of multiple two-dimensional images taken at a first time point. In the present example, the first representation 1308a may be taken at a first time point, which may occur prior to any dosing with the treatment agents. The first representation 1308a may also provide information regarding the quantity of the cells of interest, as shown in FIG. 13A.

Figure 13B:
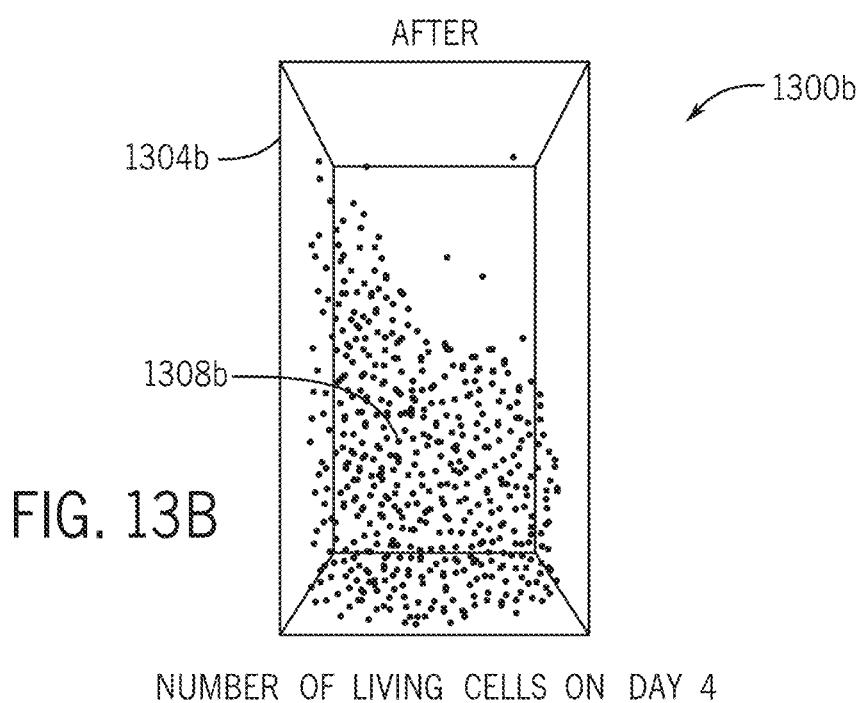
FIG. 13B depicts another chart showing a second quantity of cells at a second time point.

With reference to FIG. 13B, a chart 1300b is shown including a grid 1304b and a second representation 1308b. The grid 1304b may be a three-dimensional image that is representative of a three-dimensional space associated with the solid cell culture represented by the chart 1300a after a period of time (e.g., a second time point). For example, the second representation 1308b may be representative of a three-dimensional position of particular items of interest, such as living cells described above. In this regard, the second representation 1308b may represent a composite of multiple two-dimensional images taken at a second time point. In the present example, the second representation 1308b may be taken at a second time point, which may occur after a series of doses of the treatment agents or no treatment (e.g., with respect to a baseline/negative control). The second representation 1308b may also provide information regarding the quantity of the cells of interest, as shown in FIG. 13B.

Figure 14A:
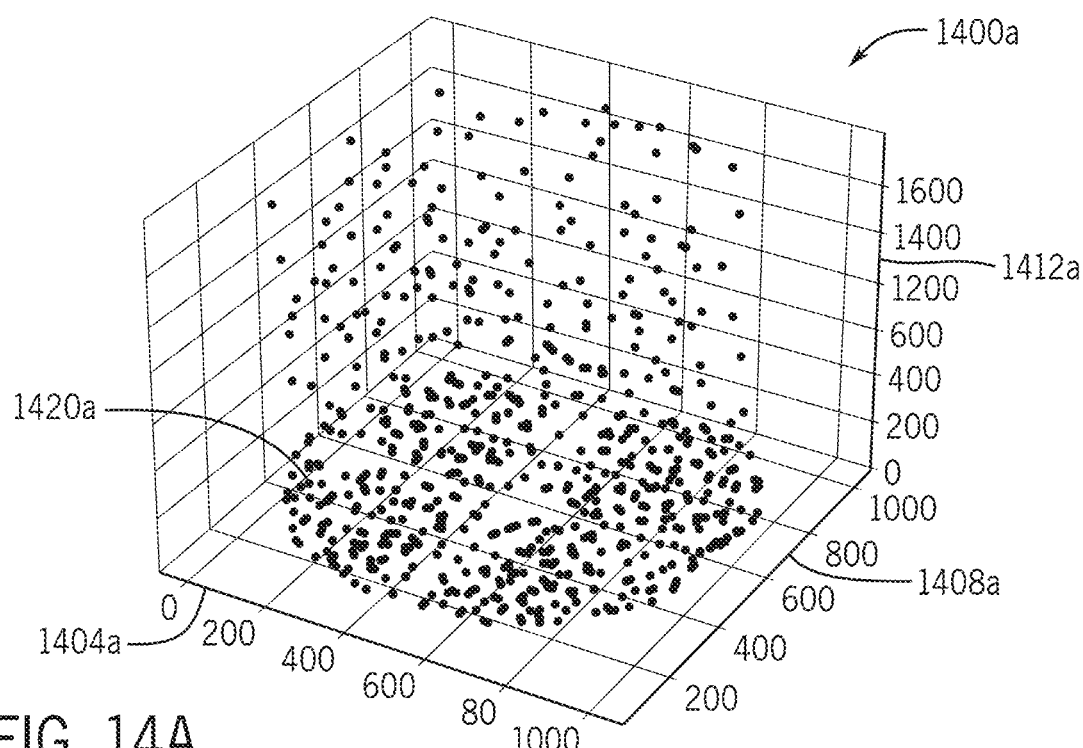
FIG. 14A depicts a chart showing a three-dimensional position of a quantity of cells at a first time point.

In some cases, it may be desirable to more precisely determine a three-dimensional position of a cell of interest at different points in time. For example, a three-dimensional position of a cell of interest may be compared between a first time and a second time to determine, among other characteristics, a cell migration vector and cell migration speed. In this regard, FIG. 14A depicts a chart 1400a showing a first distribution 1420a in a three-dimensional coordinate system defined by an axis 1404a, an axis 1408a, and an axis 1412a. The first distribution 1420a may be representative of a solid cell culture at a first time point, which may be prior to dosing. The first distribution may be produced by stitching as described herein. The chart 1400a provides information regarding the three-dimensional position of target cells in the first distribution 1420a, including distribution density. In the example of FIG. 14A, the first distribution 1420a has a higher density of cells for lower values along the axis 1412a.

Figure 14B:
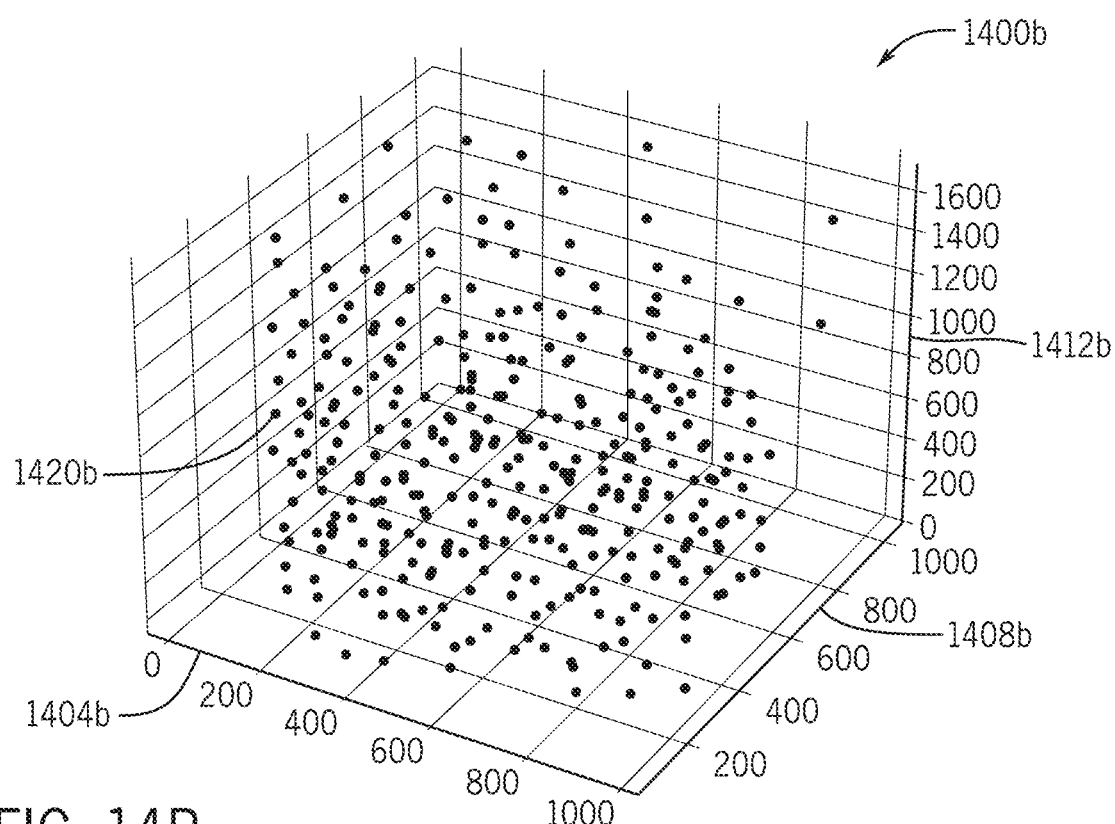
FIG. 14B depicts another chart showing a three-dimensional position of a quantity of cells at a second time point.

The solid cell culture associated with the first distribution 1420a may undergo one or more dosing producers, as described herein. The solid cell culture may be measured at a second time point subsequent to the dosing procedure. In this regard, FIG. 14B shows a chart 1400b having a second distribution 1420b in a three-dimensional coordinate system defined by an axis 1404b, an axis 1408b, and an axis 1412b. The chart 1400b provides information regarding the three-dimensional position of target cells in the second distribution 1420b, including distribution density. In the example of FIG. 14B, the second distribution 1420b has a lower density of cells in the three-dimensional coordinate system as compared with the first distribution shown in FIG. 14A.

Figure 15:
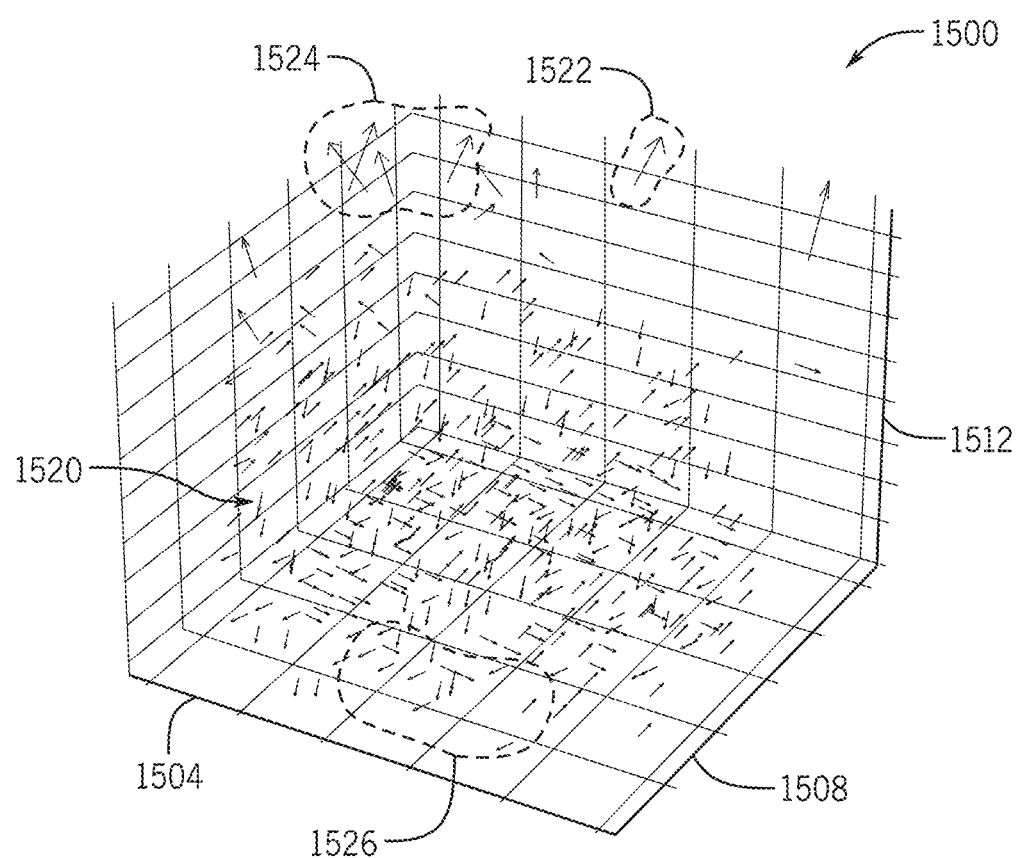
FIG. 15 depicts a chart showing a quiver plot indicative of the three-dimensional movement of cells.

FIG. 15 depicts a chart 1500 showing a quiver or vector diagram indicative of the three-dimensional movement of the quantity of cell from the three-dimensional position of FIG. 14A to the three dimensional position of FIG. 14B. For example, the three-dimensional position of a cell from the second distribution 1420b may be compared with a corresponding cell from the first distribution 1420a to determine a vector for the cell. The vector may correspond to a path of travel and/or speed for the cell between the first time point represented by the chart 1400a and the second time point represented by the chart 1400b. As such, in one example, a given cell from the first distribution 1420a may be a tail of the vector, and the corresponding cell from the second distribution 1420b may be an arrowhead of the vector. In this regard, the chart 1500 may be a three-dimensional quiver plot defined by an axis 1504, an axis 1508, and an axis 1512. A vector distribution 1520 may be plotted in the chart 1500 including vectors for one or more target cells.

The vector distribution 1520, as plotted in the chart 1500, may provide information regarding the behavior of cells during the administration of the treatment agent or no treatment (e.g., with respect to a baseline/negative control). For example, the vector distribution 1520 may include a first region 1522 having a maximum migration vector. The maximum migration vector may correspond to a cell of interest that moved the greatest amount, in speed or position, between the measured first and second time points. The vector distribution 1520 may further include a second region 1524 that may correspond to a cluster of vectors that are generally larger than other of the vector distribution 1520. In this regard, the second region 1524 may correspond to a cluster of cells that generally moved the farthest or the fastest during the administration of the treatment agents. As another example, the vector distribution 1520 may further include a third region 1526 that may correspond to a cluster of vectors that are generally smaller than other vectors of the vector distribution 1520. In this regard, the third region 1526 may correspond to a cluster of cells that generally moved the least or the slowest during the administration of the treatment. These and other trends may be identified in the chart 1500 and analyzed to determine treatment efficacy for the treatment agents.

The systems and techniques of the present disclosure may be used to monitor the response to multiple different treatment agents. For example, a solid cell culture may be prepared using any of the techniques described herein. A portion of the solid cell culture may be deposited into different microfluidic chips, such as in one or more of the six microfluidic chips shown in FIGS. 10 and 11. The microfluidic device 1000 may operate to circulate a flow of a different solution (e.g., different treatment agents) to each of the cell cultures of the microfluidic chips. As such, a solid cell culture may be defined for each chip using the different solutions or treatment agents for the cells/hydrogel initially deposited in the chip. For example, the microfluidic device 1000 may circulate a flow of different treatment agents to each chip. In some cases, one of the chips may receive no treatment agents, and just receive growth media as a control case. The response of the exposed cell cultures to the various different treatment agents may be compared to determine a treatment efficacy. For example, the determined cell characteristics for each cell culture can be compared and analyzed to determine which treatment agent was the most effective in treating the target cells.

Figure 16:
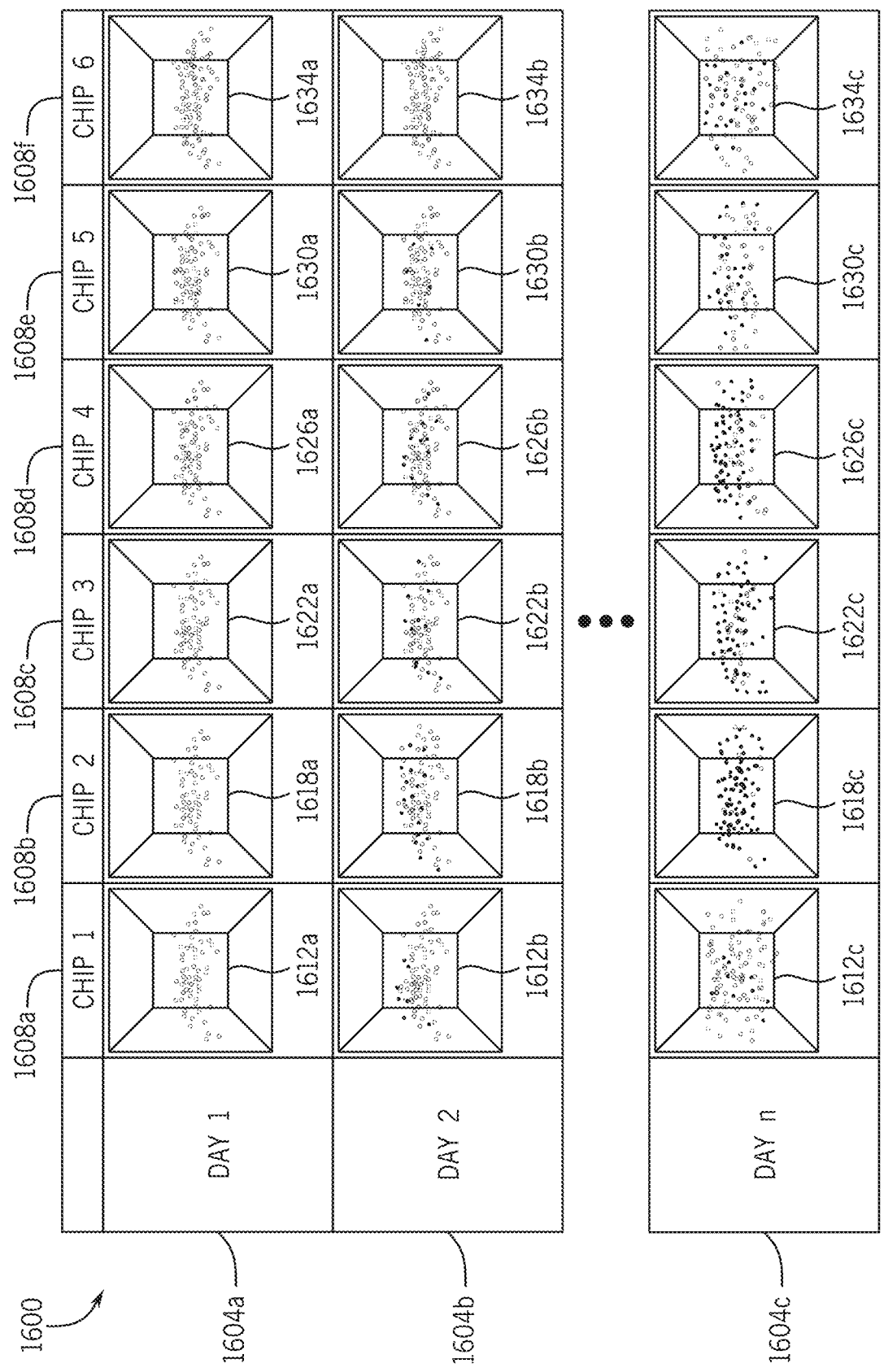
FIG. 16 depicts an example report including visualizations of different dosing operations performed on a given patient sample.

A visual representation of this comparison is presented in FIG. 16. For example, FIG. 16 depicts an example report 1600 including visualizations of different dosing operations performed on a given patient sample. The report 1600 may include information regarding the impact of a particular treatment agent for a patient sample over a period of time. In FIG. 16, the chart 1600 may include a first chip column 1608a, a second chip column 1608b, a third chip column 1608c, a fourth chip column 1608d, a fifth chip column 1608e, and a sixth chip column 1608f. In one example, each of the columns 1608a-1608f may be indicative of a different microfluidic chip (e.g., one of the microfluidic chips 800a-800f of FIGS. 10 and 11). The microfluidic chips may initially include a solid cell culture, such as any of cell cultures herein, which may include target tumor cells. The microfluidic chips may be dosed or treated with treatment agents to define an exposed cell culture in each chip. In one example, each of the microfluidic chips may be dosed with a different treatment agent in order to determine the efficacy of a particular treatment. The response of exposed cell culture of the microfluidic chips may be measured over a period of time. In this regard, the chart 1600 may include a first time point row 1604a, a second time point row 1604b, and a final time point row 1604c. In the example, of FIG. 16, the first time point row 1604a may correspond to a first day, the second time point row 1604b may correspond to a second day, and the final time point row 1604c may correspond to a subsequent day, such as a third, fourth, or fifth day.

Each microfluidic chip represented by the chip column may be imaged and analyzed for each time point represented by the time point row. For example, the microfluidic chip may be imaged to determine a color, size, position, density, and/or other property at a first given time point corresponding to the first time point row 1604a. The imaging may be a two-dimensional image or a three-dimensional image, which may be produced by stitching together the two-dimensional images. The imaging may be used to produce a representative chart 1612a, as shown in FIG. 16, which includes information for the characteristics of solid cell culture at the first time point. The chart 1612a may be substantially analogous to the charts 1300a, 1300b described above for FIGS. 13A and 13B. Further, the microfluidic chip may be subsequently imaged at a second given time point, such as subsequent to a round of dosing via the treatment agents, and which may correspond to the second time point row 1604b. Accordingly, the imaging may be used to produce a representative chart 1612b, which includes information for the characteristics of the solid cell culture at the second time point. Further, the microfluidic chip may be subsequently imaged at a third given time point, such as subsequent to another round of dosing via the treatment agents, and which may correspond to the final time point row 1604c. Accordingly, the imaging may be used to produce a representative chart 1612c, which includes information for the characteristics of the solid cell culture at the final time point.

A response of the solid cell culture of the first microfluidic chip may be analyzed over time to determine a treatment efficacy for the treatment agents administered to the first microfluidic chip, as described herein. The chart 1600 and corresponding analysis may allow for the comparison of the treatment efficacy across multiple different treatment agents, including combinations of agents dosed simultaneously and/or sequentially, for the cell culture. For example, and substantially analogous to the first chip column 1608a, the second chip column 1608b may include a representative chart 1618a at the first time point row 1604a, a representative chart 1618b at the second time point row 1604b, and a representative chart 1618c at the final time point row 1604c. Further, and substantially analogous to the first chip column 1608a, the third chip column 1608c may include a representative chart 1622a at the first time point row 1604a, a representative chart 1622b at the second time point row 1604b, and a representative chart 1622c at the final time point row 1604c. Further, and substantially analogous to the first chip column 1608a, the fourth chip column 1608d may include a representative chart 1626a at the first time point row 1604a, a representative chart 1626b at the second time point row 1604b, and a representative chart 1626c at the final time point row 1604c. Further, and substantially analogous to the first chip column 1608a, the fifth chip column 1608e may include a representative chart 1630a at the first time point row 1604a, a representative chart 1630b at the second time point row 1604b, and a representative chart 1630c at the final time point row 1604c. Further, and substantially analogous to the first chip column 1608a, the sixth chip column 1608f may include a representative chart 1634a at the first time point row 1604a, a representative chart 1634b at the second time point row 1604b, and a representative chart 1634c at the final time point row 1604c.

With respect to the final time point row 1604c, the report 1600 includes representative charts 1612c, 1618c, 1622c, 1626c, 1630c, 1634c for each of the microfluidic chips at the final time point. The final time point may be representative of a conclusion of the dosing of the various treatment agents. In this regard, the information of each of the representative charts 1612c, 1618c, 1622c, 1626c, 1630c, 1634c may be compared to determine which cell culture exhibits the best or most effective response to a given treatment agent with respect to the control/baseline. For example, the representative chart 1612c may show information corresponding to a response of the cell culture to a first treatment agent at the final time point, the representative chart 1618c may show information corresponding to a response of the cell culture to a second treatment agent at the final time point, the representative chart 1622c may show information corresponding to a response of the cell culture to a third treatment agent at the final time point, the representative chart 1626c may show information corresponding to a response of the cell culture to a fourth treatment agent at the final time point, the representative chart 1630c may show information corresponding to a response of the cell culture to a fifth treatment agent at the final time point, the representative chart 1634c may show information corresponding to a response of the cell culture to a sixth treatment agent (or a control with no treatment agent, which could apply to any single or multiple microfluidic chips) at the final time point. In this regard, characteristics such as target cell color, size, density, count, and so on, may be compared across each of the representations shown in the final time point row 1604c to determine a treatment efficacy. As one example, where the representation shows a lower tumor cell density or live cell count for the final time point row 1604c, the treatment agent that was used to for the treatment of the microfluidic chip that resulted in the representation may be determined to have the high treatment efficacy among the treatment agents.

Figure 17:
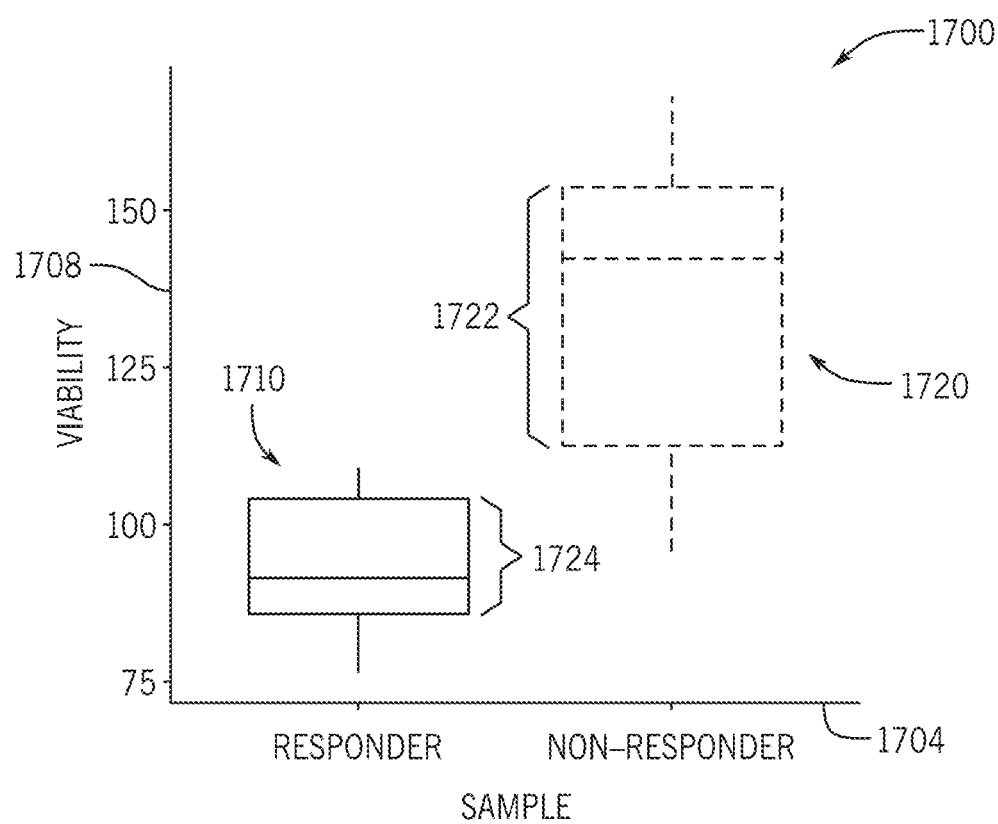
FIG. 17 depicts a chart showing a distribution of cancerous cell viability based on one or more dosing operations described herein.

For example, the response of a cell culture to a given treatment agent may be used to determine cell viability. For example, the viability of both responders and non-responders may be determined and plotted in order to determine an efficacy of treatment. With reference to FIG. 17, a chart 1700 is depicted showing cell viability with respect to responders, such as a BRCA mutated, and non-responders, such as BRCA wild-type. With reference to FIG. 17, the chart 1700 includes a data set axis 1704 and a viability axis 1708. A first distribution 1710 having a first spread 1724 is shown alongside a second distribution 1720 having a second spread 1722. The viability of the responders of the first distribution 1710 may be compared to the viability of the non-responders of the second distribution 1720 with the chart 1700 in order to provide information to assist in determining treatment efficacy.

To facilitate the reader's understanding of the various functionalities of the embodiments discussed herein, reference is now made to the flow diagram in FIGS. 18-21, which illustrates process 1800, 1900, 2000, 2100, respectively. While specific steps (and orders of steps) of the methods presented herein have been illustrated and will be discussed, other methods (including more, fewer, or different steps than those illustrated) consistent with the teachings presented herein are also envisioned and encompassed with the present disclosure.

Figure 18:
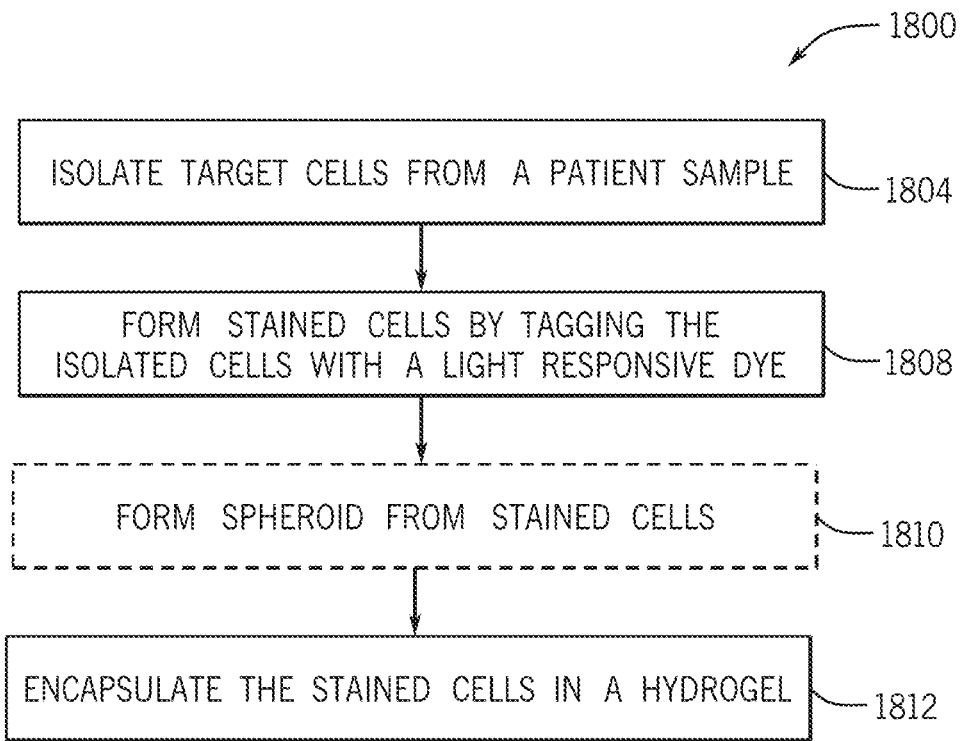
FIG. 18 depicts a flow diagram for forming a cell culture.

With reference to FIG. 18, a process 1800 is disclosed. The process 1800 is directed to a method of forming a solid cell culture, such as that described with respect to FIG. 2. At operation 1804, target cells are isolated from a patient sample. For example, and with reference to FIGS. 2 and 3, a patient sample 304 may be obtained. The sample 304 may arrive at a lab, and include samples containing a tumor of various cancer types. A digestion enzyme-based cell isolation kit, blood lysis solution and other selecting or filtering steps may be used to isolate viable cells while removing blood and contaminants. The output may be a viable mixed cell population containing the various cells from the primary tumor, including cancer cells, normal/non-transformed cells, stromal cells and immune cells.

At operation 1808, stained cells are formed from the isolated cells by staining the target cells with a light-responsive dye. For example, and with reference to FIGS. 2, 4, and 7, cells may be stained with one or both of a live cell dye and a dead cell staining dye. The dyes may be light-responsive dyes. For example, the cells may be stained with a first light-responsive dye to facilitate live cell tracking. The cells may be further stained with a second light-responsive dye to facilitate dead cell tracking. In some cases, the light-responsive dye is configured to cause a color change in the stained cell when the stained cell transitions from a living cell to a dead cell.

At operation 1810, a spheroid may optionally be formed from the stained cells. The spheroid or organoid may also include cancer cells, normal/non-transformed cells, stromal cells, and/or immune cells, which are formed from a patient-derived tissue or tumor sample. Tissue slices, cores, surgical resections, xenografts, and/or biopsies may also be used.

At operation 1812, the stained cells are encapsulated. For example, and with reference to FIGS. 2 and 6, the stained cells, such as isolated cells (or spheroids formed from operation 1810) may be included in the hydrogel 608. The hydrogel 608 may be configured to replicate components of human tissue, which may facilitate cell growth. For example, and as described herein, hyaluronic acid and collagen may be used to mimic core components of human tissue extracellular matrices and disease-specific cell niches, like those found in breast tumors.

It will be appreciated that various types of cell cultures may be used and/or formed in conjunction with the process 1800 of FIG. 18. For example, the culturing of process 1800 may include culturing dissociated cells in the hydrogel. The dissociated cells may be formed via two-dimensional or three-dimensional cell cultures. In some cases, the dissociated cells may be a single population of cells, whereas in other cases, multiple cell types may be used. For example, the dissociated cells may be cancer, normal/non-transformed cells, stromal, and/or immune cells, as one example, derived from a tissue or tumor sample.

Figure 19:
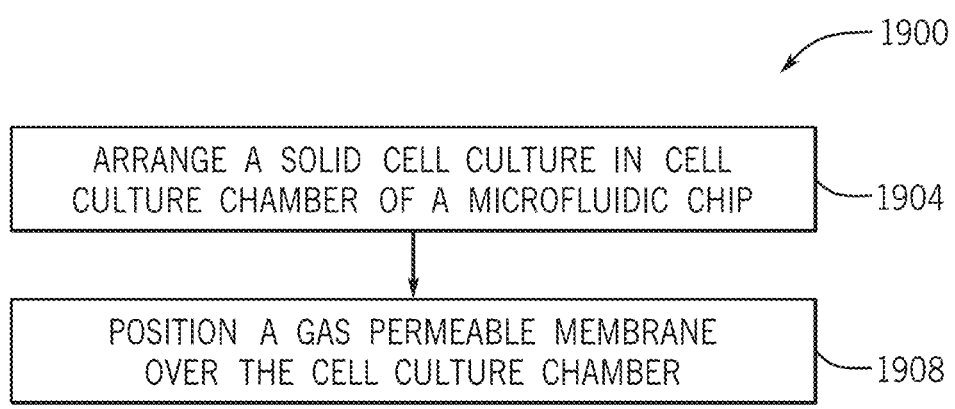
FIG. 19 depicts a flow diagram for loading a microfluidic chip.

With reference to FIG. 19, a process 1900 is disclosed. The process 1900 is directed to a method of loading a microfluidic chip, such as that shown above with respect to FIGS. 9A-9F. At operation 1904, a solid cell culture is arranged in a cell culture chamber of a microfluidic chip. The microfluidic chip includes a body defining a cell culture chamber and a channel that traverses the cell culture chamber and extends between an inlet and an outlet of the microfluidic chip. For example, and with reference to FIGS. 9B and 9C, the solid cell culture 910 is arranged in the first cell culture chamber 814 of the microfluidic chip 800. The microfluidic chip 800 includes the body 801 that defines the first cell culture chamber 814 and the channel 862 that runs along or adjacent the first cell culture chamber 814 and extends between the inlet feature 843*a* and the outlet feature 843*b*.

At operation 1908, a gas permeable membrane is positioned over a volume containing the cell culture chamber while the inlet and outlet remain exposed for coupling to a circulation system. For example, and with reference to FIGS. 9D and 9E, the gas permeable layer 852 is positioned on to the body 801. The gas permeable layer 852 may be adhered to the body 801 via the adhesive surface 835. As shown in FIG. 9E, the gas permeable layer 852 may cover both the first volume 864 and the second volume 866, containing the first cell culture chamber 814 and the second cell culture chamber 816, while allowing the first cell culture chamber 814 and the second cell culture chamber 816 to be exposed to gas in a surrounding atmosphere of the microfluidic chip 800.

Figure 20:
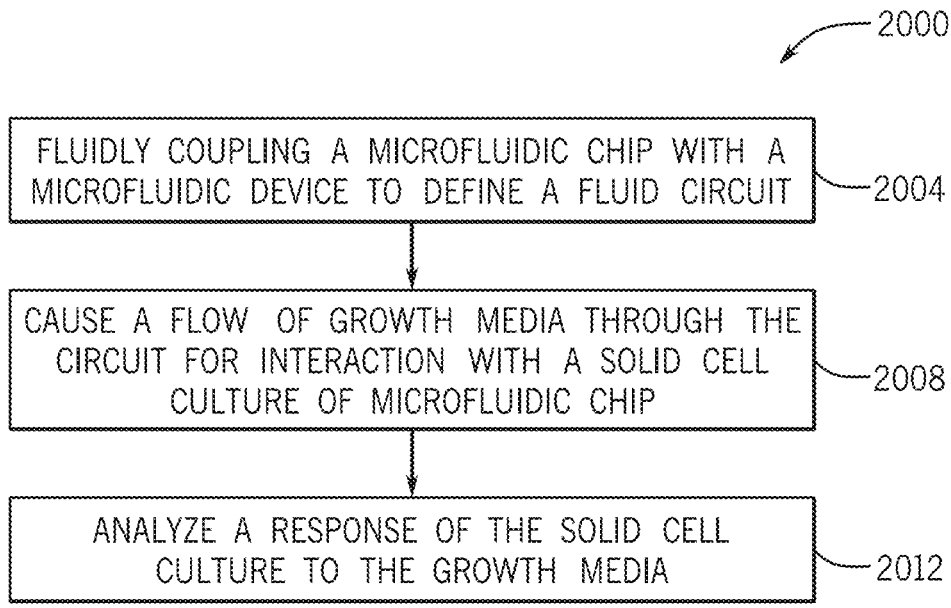
FIG. 20 depicts a flow diagram for dosing and imaging a culture of microfluidic chip.

With reference to FIG. 20, a process 2000 is disclosed. The process 2000 is directed to a method of operating a microfluidic chip. At operation 2004, a microfluidic chip is fluidly coupled with a microfluidic device to define a fluid circuit between the microfluidic chip, a flow restrictor, a reservoir, and a pump. The microfluidic chip including a cell culture, the reservoir including a media. For example, and with reference to FIGS. 10 and 11, microfluidic chips 800*a*-800*f* may be fluidly coupled with the microfluidic device 1000. The microfluidic device 1000 may operate to define fluid circuits 1002*a*-1002*f* between each respective microfluidic chip 800*a*-800*f* and a corresponding one of the reservoirs 1022*a*-1022*f*.

At operation 2008, a flow of the media is caused through the circuit such that the media interacts with the solid cell culture of the microfluidic chip to define an exposed cell culture in the microfluidic chip. For example, and with reference to FIGS. 10 and 11, the microfluidic device 1000 may operate the pump 1030 to cause a flow of media through each of the fluid circuits 1002*a*-1002*f*. The pump 1030 may be configured to control a flow of circulation through each of the fluid circuits 1002*a*-100*f* separately. This may allow the microfluidic device 1000 to administer separate treatment agents to each of the microfluidic chips 800*a*-800*f* such a response to each of the different treatment agents may be measured.

For example, at operation 2012, a response of the solid cell culture to the media is analyzed. For example, and with reference to FIGS. 11, 13A, 13B and 16, a given microfluidic chip may be removed and fluidly uncoupled from the microfluidic device 1000. The microfluidic chip may be imaged or otherwise analyzed for the given time point at which the microfluidic chip is fluidly uncoupled. As one example, the microfluidic chip may undergo a process of fluorescence microscopy. Fluorescence microscopy may capture images of the cell culture of the given microfluidic chip under conditions in which the light-responsive dye allows for detection of target cells, e.g., the detection of dead cells and/or living cells. Confocal microscopy, brightfield microscopy, and lattice sheet microscopy may all be used, in addition to other imaging techniques. In one example, the images may be two-dimensional images. As described herein, the two-dimensional images may be captured in a manner that is representative of layers of the cell culture. The layers may be stacked on one another or stitched together to form a three-dimensional image.

In another example, the given microfluidic chip may be fluidly coupled to the microfluidic device again to administer further media, including additional treatment agents. In this regard, the method 2000 may further include causing another flow of the media through the circuit, at a second time point, such that the media interacts with the cell culture of the microfluidic chip, and analyzing a subsequent response of the cell culture to the media. Analyzing of the subsequent response of the cell culture may include imaging, as described, which is used to generate a two-dimensional or three-dimensional image of the cell culture. The imaging of the cell culture at the first and second time points may be analyzed to determine a treatment efficacy. As described herein, additional time points may also be analyzed. As one example, the method 2000 may include analyzing the image at the first time point to determine a first live/dead cell population quantity. The method 2000 may further include analyzing the image at the second time point to determine a second live/dead cell population quantity. The first cell population quantity and the second cell population quantity may, in turn, be compared to determine change in cell population quantity indicative of a treatment efficacy. As another example, the method 2000 may include analyzing the image at the first time point to determine a first cell population position and analyzing the image at the second time point to determine a second cell population position. The first cell population position and the second cell population positon may, in turn, be compared to determine a change in cell population position indicative of a treatment efficacy.

Figure 21:
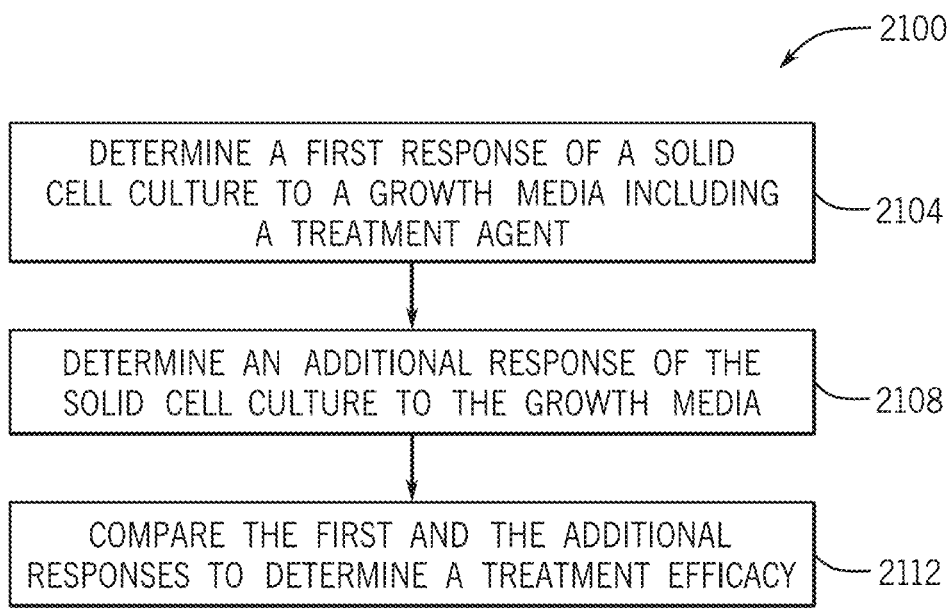
FIG. 21 depicts a flow diagram for determining a treatment efficacy.

With reference to FIG. 21, a process 2100 is disclosed. The process 2100 is directed to analyzing a solid cell culture over time. The process 2100 may be executed fully, or in part, using the computing device 2200 described below with reference to FIG. 22. For example, various operations may be performed after the computing device 2200 (or multiple computing devices 2200) receive data from the system (e.g., microfluidic system and chips) and utilize this data to make assessments regarding treatment efficacy and patient response. At operation 2104, a first response of a solid cell culture to a growth media, including a treatment agent, is determined. The solid cell culture is held in a cell culture chamber of a microfluidic chip. For example, and with reference to FIGS. 9B and 13A, a first response of the cell culture 910 may be determined at a first time point. The first response may be determined by executing instructions of a non-transitory computer-readable media with one or more processing elements of the computing device 2200. For example, the cell culture 910 may be analyzed, using the computing device 2200, to determine a cell color, quantity, size, density and/or other characteristics at a first point in time, which may be represented by the first representation 1308a of FIG. 13A. The first response may be a response of the cell culture 910 prior to a dosing with a treatment agent. More specifically, in one implementation, the computing device 2200 may receive data corresponding to images captured by one or more of the components described herein, where the images may be analyzed to determine cell color, quantity, size, and density, e.g., by utilizing image analysis or computer vision algorithms that can identify pixel colors and distribution corresponding to the cells.

At operation 2108, additional responses of the cell culture to the media is determined. For example, and with reference to FIGS. 9B and 13B, additional responses of the cell culture 910 may be determined at a second time point, third time point, fourth time point, fifth time point, and so on. The additional responses may be determined by executing instructions of a non-transitory computer-readable media with one or more processing elements of the computing device 2200. For example, the cell culture 910 may be analyzed, using the computing device 2200, to determine a cell quantity, color, size, density and/or other characteristics at substantially any subsequent time point, which may be represented by one or more of the distributions of FIG. 16. The additional responses may be a response of the cell culture 910 subsequent to a dosing with a treatment agent. In some implementations, the computing device 2200 may utilize computer vision and/image analysis algorithms that can identify the cells within one or more images captured and can extract information, such as hue, intensity, or the like, that can be utilized to determine the response information.

At operation 2112, the first and the additional responses (e.g., a second response, a third response, a fourth response, a fifth response, and so on) are compared to determined treatment efficacy. The first and the additional responses may be compared by executing instructions of a non-transitory computer-readable media with one or more processing elements of the computing device 2200, such as one or more image analysis or computer vision algorithms as described above. For example, and with reference to FIG. 16, as one example, the color, size, quantity, density and/or other characteristics of the cell cultures may be compared, using the computing device 2200, between the first time point and any of the subsequently measured time points. A relative increase or decrease in one or more of these characteristics may be indicative of an efficacy of the treatment provided for by the corresponding treatment agent. Other properties may also be measured and compared with respect to the first and second responses, including, but not limited to, a color of the cell culture, a pixel intensity of an image of the cell culture, a shape of cell culture, a size of cell culture, a position of cells of the cell culture, or a quantity of cell of the cell culture.

In this regard, the first and/or second response may include capturing an image, such as a two-dimensional or three-dimensional image of the cell. The method 2100 may further include determining one or more of a cell viability, a cell proliferation, a cell position from the image. With respect to spheroids/organoids, the method 2100 may further include determining a cell viability using a color and/or a color ratio to predict treatment response. For example, the image analysis may extract hue and/or intensity information to correlate the same to cell viability, based on a color mapping, machine learning, look up table, or the like. However, the method for determining the cell viability may vary based on the type of image analysis or computer vision algorithms utilized.

The first color indicative of live cells (e.g., a red color) and a second color indicative of dead cells (e.g., a green color) can be compared at one, two, or more time points to determine, for example, a cell death within a spheroid. In other words, the system may analyze hue information at various pixel locations over time, which can be correlated to cell death within the spheroid. Such information may be used as a predictive metric (e.g., ratio of live and dead cells). In other cases, other techniques may be used to determine a cell viability. The method 2100 may further include predicting a patient response to the treatment agent based on one or more of cell viability, cell proliferation, or the cell position, for example, as described herein with respect to operation 252 of FIG. 2. In some cases, as described herein, an image indicative of the first response may be compared, using the computing device 2200, to an image indicative of the second response to facilitate the prediction of the patient response. For example, data from the two images may be analyzed by the computer device 2200 to determine via image analysis distinctions in the responses that indicate one response may be better or more improved in terms of cancer cell death as compared to the other. In this regard, the method 2100 may further include comparing the images to determine one or more of a cell migration speed or a cell migration distance for one or more cells over time. For example, pixel analysis may be used to generate distance vectors that may then be compared in length or dimension to determine cell migration distances. The cell migration speed and/or the cell migration distance over time may be indicative of a patient response to the treatment agent. Maximum or minimum of migration vectors or speeds may also be computed in this regard. In some cases, the cell migration speed and/or the cell migration distance may be determined with respect to a subset of the most aggressive cells, including but not limited to, the 5% most aggressive cells of the cell culture, the 2% most aggressive cells of the cell culture, the 1% most aggressive cells of the cell culture, among other subsets. Additionally or alternatively, the cell migration speed and/or the cell migration distance may be computed with respect to a subset of cells expressing a specific bio marker.

The analysis of operation 2112 may be performed with respect to a single cell. For example, the change in position of a single cell may be tracked between first time point and second time point. In this example, a cell may be tagged or otherwise identified in one or more images and then tracked over time in determines of movement between different image frames. In other cases, the operation 2112 may be performed with respect to a weighted cell measurement. For example, weighting factors may be used based on an association of how much each characteristic of the cell culture affects a treatment response prediction. As an illustration, the likelihood of a patient responding to treatment A may be based on a patient having a minimum score of X. The score X is calculated by having three quarters of the score coming from the cell viability of the culture and one quarter of the score coming from the cell migration speed of that culture. The weighted cell measurement may be a composite score of multiple individual measurements (e.g., cell viability, migration distance, and so on).

In some cases, the images of the first and second response described above may be images of spheroid or organoids. In this regard, a radius, diameter or circumference of the spheroid or organoid may be measured or determined using the images and compared across multiple time points. For example, the computing device may analyze the image to determine an approximate perimeter for the spheroid or organoid and then calculate a circumference, diameter, or other measurements with respect to an estimated area and/or volume of the spheroid or organoid. Additionally or alternatively, dissociated/single cell analysis may be accomplished using similar techniques. For example, dissociated/single cells may be tracked and measured using substantially any of the associated metrics, as described herein. As illustrative examples, a count and/or a position of a single cells that leave the spheroid, a migration distance, a migration speed, and so on may be determined and analyzed according to the techniques described herein for determining treatment efficacy. In this regard, the method 2100 may include predicting a patient response to the treatment agent based on a comparison of the first radius or the first diameter with the second radius or the second diameter of the respective first and second images. Additionally or alternatively, surgical resections, tissue slices, xenografts, and/or core needle biopsies may be used, which may have a length, width, and height. In this regard, the length, width, or height of the tissue slices, surgical resections, xenografts, and/or core needle biopsies may be measured using the images and compared across multiple time points. In this regard, the method 2100 may include predicting a patient response to the treatment agent based on a comparison of the first length, the first width, or the first height with the second length, the second width, or the second height of the respective first and second images.

Figure 22:
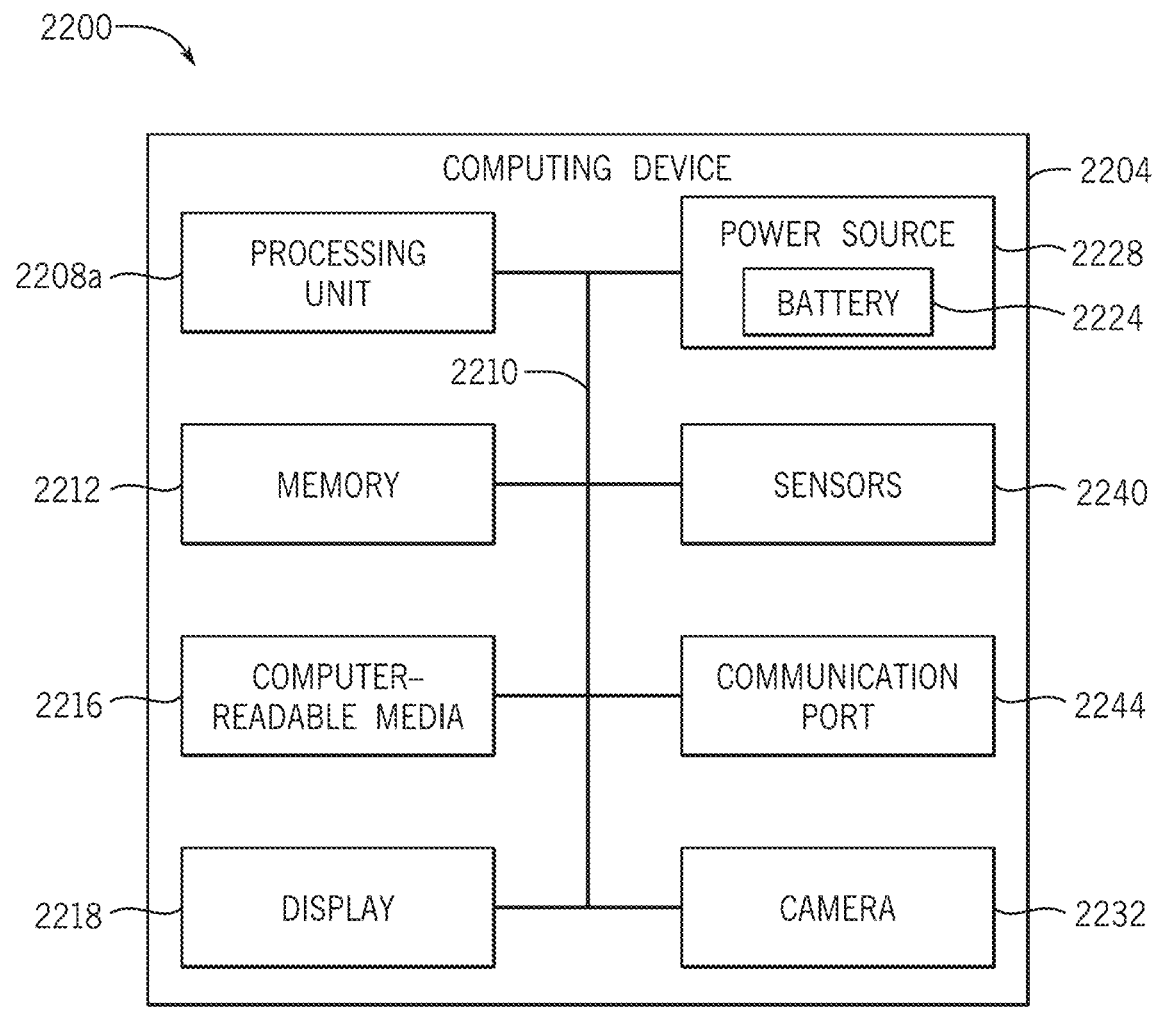
FIG. 22 depicts a functional block diagram of a system including a computing device.

FIG. 22 presents an example computing device 2200. The schematic representation in FIG. 22 of the computing device 2200 may include systems, components, modules, assemblies, and subassemblies configured to implement or execute any of the techniques and processes described herein. In this regard, the computing device 2200 may include any appropriate hardware (e.g., computing devices, data centers, switches), software (e.g., applications, system programs, engines), network components (e.g., communication paths, interfaces, routers) and the like (not necessarily shown in the interest of clarity) for use in facilitating any appropriate operations disclosed herein.

As shown in FIG. 22, the computing device 2200 may include a processing unit or element 2208a operatively connected to computer memory 2212 and computer-readable media 2216. The processing unit 2208a may be operatively connected to the memory 2212 and computer-readable media 2216 components via an electronic bus or bridge (e.g., such as system bus 2210). The processing unit 2208a may include one or more computer processors or microcontrollers that are configured to perform operations in response to computer-readable instructions. The processing element 2208a may be a central processing unit of the computing device 2200. Additionally or alternatively, the processing unit 2208a may be other processors within the device including application specific integrated chips (ASIC) and other microcontroller devices.

The memory 2212 may include a variety of types of non-transitory computer-readable storage media, including, for example, random access memory (RAM), read-only memory (ROM), erasable programmable memory (e.g., EPROM and EEPROM), or flash memory. The memory 2212 is configured to store computer-readable instructions, sensor values, and other persistent software elements. Computer-readable media 2216 may also include a variety of types of non-transitory computer-readable storage media including, for example, a hard-drive storage device, a solid state storage device, a portable magnetic storage device, or other similar device. The computer-readable media 2216 may also be configured to store computer-readable instructions, sensor values, and other persistent software elements.

In this example, the processing unit 2208a is operable to read computer-readable instructions stored on the memory 2212 and/or computer-readable media 2216. The computer-readable instructions may adapt the processing unit 2208a to perform the operations or functions described above with respect to FIGS. 1-21. The computer-readable instructions may be provided as a computer-program product, software application, or the like.

As shown in FIG. 22, the computing device 2200 may also include a display 2218. The display 2218 may include a liquid-crystal display (LCD), organic light emitting diode (OLED) display, light emitting diode (LED) display, or the like. The computing device 2200 may also include a battery 2224 that is configured to provide electrical power to the components of the computing device 2200. The battery 2224 may include one or more power storage cells that are linked together to provide an internal supply of electrical power. In this regard, the battery 2224 may be a component of a power source 2228 (e.g., including a charging system or other circuitry that supplies electrical power to components of the computing device 2200).

The computing device 2200 may also include one or more sensors 2240 that may be used to detect a touch and/or force input, environmental condition, orientation, position, or some other aspect of the computing device 2200. The computing device 2200 may also include a camera 2232 that is configured to capture a digital image or other optical data. The computing device 2200 may also include a communication port 2244 that is configured to transmit and/or receive signals or electrical communication from an external or separate device. The communication port 2244 may be configured to couple to an external device via a cable, adaptor, or other type of electrical connector. In some embodiments, the communication port 2244 may be used to couple the computing device 2200 with a computing device and/or other appropriate accessories configured to send and/or receive electrical signals.

Other examples and implementations are within the scope and spirit of the disclosure and appended claims. For example, features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A method of analyzing an ex vivo solid cell culture over time, the method comprising:
    determining a first response of a solid cell culture to a growth media including a treatment agent, the solid cell culture held in a cell culture chamber of a microfluidic chip by determining first location coordinates of at least a first single cell of the solid cell culture including a first x location coordinate, a first y location coordinate, and a first z location coordinate;
    determining a second response of the solid cell culture to the growth media by determining second location coordinates of the at least first single cell of the solid cell culture including a second x location coordinate, a second y location coordinate, and a second z location coordinate; and
    comparing the first response and the second response to determine a treatment efficacy,
    wherein comparing the first response and the second response comprises comparing the first location coordinates to the second location coordinates to determine a difference between the first location coordinates and the second location coordinates, and wherein the difference between the first location coordinates and the second location coordinates is between at least one of the first x location coordinate and the second x location coordinate, the first y location coordinate and the second y location coordinate, or the first z location coordinate and the second z location coordinate, the difference representing a cell migration distance of the at least first single cell over time.

2. The method of claim 1, wherein one or both of the first response or the second response comprises at least one of a color or multiple colors of the solid cell culture, a pixel intensity of an image of the solid cell culture, a shape of the solid cell culture, a size of the solid cell culture, a position of cells of the solid cell culture, or a quantity of cells of the solid cell culture.

3. The method of claim 1, wherein the treatment efficacy is indicative of a viability of cells of the solid cell culture in response to the treatment agent.

4. The method of claim 1, wherein determining the first response comprises capturing an image of the solid cell culture.

5. The method of claim 4, further comprising
    determining a cell viability from the image, and
    predicting a patient response to the treatment agent based on the cell viability.

6. The method of claim 4, further comprising
    determining a cell proliferation from the image, and
    predicting a patient response to the treatment agent based on the cell proliferation.

7. The method of claim 4, further comprising
    determining a cell position from the image, and
    predicting a patient response to the treatment agent based on the cell position.

8. The method of claim 4, wherein
    the image is a first image, and
    determining the second response comprises capturing a second image of the solid cell culture.

9. The method of The method of wherein determining the cell migration distance of the at least first single cell over time includes comparing the first image and the second image, and the method further comprises predicting a patient response to the treatment agent using the cell migration distance.

10. The method of claim 8, further comprising comparing the first image and the second image to determine a cell migration speed of the at least first single cell of the solid cell culture over time, and predicting a patient response to the treatment agent using the cell migration speed.

11. The method of claim 8, further comprising
    comparing the first image and the second image to determine a migration distance of a plurality of cells that define all cells or a subset of cells of the solid cell culture over time, and
    predicting a patient response to the treatment agent using the migration distance.

12. The method of claim 8, further comprising
    comparing the first image and the second image to determine a migration speed of a plurality of cells that define all cells or a subset of cells of the solid cell culture over time, and
    predicting a patient response to the treatment agent using the migration speed.

13. The method of claim 11, wherein the plurality of cells comprises the subset of cells being the 5% most aggressive cells of the plurality of cells.

14. The method of claim 11, wherein the plurality of cells comprises the subset of cells being less than 2% most aggressive cells of the plurality of cells.

15. The method of claim 11, wherein the plurality of cells comprises the subset of cells expressing a specific biomarker.

16. The method of claim 8, further comprising
    comparing the first image and the second image to determine a cell having a maximum migration vector of the solid cell culture over time, and
    predicting a patient response to the treatment agent using the maximum migration vector.

17. The method of claim 8, further comprising
    comparing the first image and the second image to determine a cell having a maximum migration speed of the solid cell culture over time, and
    predicting a patient response to the treatment agent using the maximum migration speed.

18. The method of claim 1, wherein the determining the first response comprises determining characteristics of the at least first single cell at a first time, the determining the second response comprises determining characteristics of the at least first single cell at a second time subsequent to the first time, and predicting a patient response to the treatment agent based on a comparison of the measured characteristics of the at least first single cell at the first time and the second time.

19. The method of claim 8, wherein
one or both of the first image or the second image comprises a composite and/or a weighted cell measurement, and
the method further comprises predicting a patient response to the treatment agent based on the composite and/or weighted cell measurement.

20. The method of claim 19, wherein
the first image comprises a first composite and/or weighted cell measurement, the second image comprises a second composite and/or weighted cell measurement, and
predicting a patient response to the treatment agent based on a comparison of the first composite and/or weighted cell measurement and the second composite and/or weighted cell measurement.

21. The method of claim 8, wherein
one or both of the first image or the second image comprises information associated with a radius, a diameter, or a circumference of a spheroid or an organoid, and
the method further comprises predicting a patient response to the treatment agent based on the radius, the diameter, or the circumference of the spheroid or the organoid.

22. The method of claim 21, wherein
the first image comprises a first radius, a first diameter, or a first circumference of the spheroid or the an organoid,
the second image comprises a second radius, a second diameter, or a second circumference of the spheroid or the organoid, and
predicting a patient response to the treatment agent based on a comparison of the first radius, the first diameter, or the first circumference with the second radius, the second diameter, or the second circumference.

23. The method of claim 8, wherein
one or both of the first image or the second image comprises information associated with one or more of a length, a width, or a height of a surgical resection, tissue slice, xenograft, or core needle biopsy, and
the method further comprises predicting a patient response to the treatment agent based on the length, a width, or a height of a surgical resection, tissue slice, xenograft, or core needle biopsy.

24. The method of claim 23, wherein
the first image comprises a first length, a first width, or a first height of a surgical resection, tissue slice, xenograft, or core needle biopsy,
the second image comprises a second length, a second width, or a second height of the surgical resection, tissue slice, xenograft, or core needle biopsy, and
predicting a patient response to the treatment agent based on a comparison of the first length, the first width, or the first height with the second length, the second width, or the second height.

25. The method of claim 1, wherein the comparing comprises executing instructions of a non-transitory computer-readable media, with one or more processing elements of a computer, to determine the treatment efficacy, wherein the treatment efficacy corresponds to a treatment option applied to a patient from which the solid cell culture originated.

26. The method of claim 1, further comprising:
determining a third response of the solid cell culture to the growth media; and
comparing the first, second and/or third responses to determine a treatment efficacy.

27. The method of claim 26, further comprising:
determining a fourth response of the solid cell culture to the growth media; and
comparing the first, second, third and/or fourth responses to determine a treatment efficacy.

28. The method of claim 27, further comprising:
determining a fifth response of the solid cell culture to the growth media; and
comparing the first, second, third, fourth and/or fifth responses to determine a treatment efficacy.

29. The method of claim 1, further comprising forming the solid cell culture by:
isolating target cells from a patient sample;
forming stained cells from the isolated cells by staining the isolated cells with a light-responsive dye that causes a color change in the stained cell when the stained cell transitions from a living cell to a dead cell; and
encapsulating the stained cells in a hydrogel.

* * * * *